(12) United States Patent
Minamizato et al.

(10) Patent No.: US 10,413,157 B2
(45) Date of Patent: Sep. 17, 2019

(54) ENDOSCOPE SYSTEM WITH IMAGE PASTING ON PLANAR MODEL

(71) Applicant: OLYMPUS CORPORATION, Tokyo (JP)

(72) Inventors: Miho Minamizato, Tachikawa (JP); Jun Hasegawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 454 days.

(21) Appl. No.: 15/080,768

(22) Filed: Mar. 25, 2016

(65) Prior Publication Data

US 2016/0278612 A1   Sep. 29, 2016

Related U.S. Application Data

(63) Continuation of application No. PCT/JP2014/075099, filed on Sep. 22, 2014.

(30) Foreign Application Priority Data

Sep. 27, 2013   (JP) ................. 2013-201898

(51) Int. Cl.
| | | |
|---|---|---|
| *A61B 1/00* | (2006.01) | |
| *A61B 1/05* | (2006.01) | |
| *A61B 1/005* | (2006.01) | |
| *A61B 1/06* | (2006.01) | |
| *A61B 1/303* | (2006.01) | |
| *A61B 1/307* | (2006.01) | |
| *A61B 5/06* | (2006.01) | |

(52) U.S. Cl.
CPC .......... *A61B 1/00009* (2013.01); *A61B 1/005* (2013.01); *A61B 1/00045* (2013.01); *A61B 1/051* (2013.01); *A61B 1/0638* (2013.01); *A61B 1/0646* (2013.01); *A61B 1/0684* (2013.01); *A61B 1/303* (2013.01); *A61B 1/307* (2013.01); *A61B 5/062* (2013.01)

(58) Field of Classification Search
CPC . A61B 1/00009; A61B 1/00045; A61B 1/005; A61B 1/051; A61B 1/0638; A61B 1/0646; A61B 1/0684; A61B 1/303; A61B 1/307; A61B 5/062
USPC ........ 600/103, 109, 113, 117, 118, 160, 173, 600/176, 182
See application file for complete search history.

(56) References Cited

U.S. PATENT DOCUMENTS

| | | | | |
|---|---|---|---|---|
| 6,059,718 A | * | 5/2000 | Taniguchi ............ | A61B 1/0005 600/117 |
| 6,346,940 B1 | * | 2/2002 | Fukunaga ............... | G06T 15/20 345/420 |
| 6,351,573 B1 | * | 2/2002 | Schneider ............. | G06F 19/321 382/128 |
| 7,491,198 B2 | * | 2/2009 | Kockro ................... | A61B 90/36 606/1 |
| 2004/0070822 A1 | * | 4/2004 | Shioda ...................... | A61B 1/04 359/372 |
| 2004/0097806 A1 | * | 5/2004 | Hunter ............... | A61B 1/00071 600/434 |
| 2004/0116775 A1 | | 6/2004 | Taniguchi et al. | |
| 2005/0054895 A1 | * | 3/2005 | Hoeg ..................... | A61B 90/36 600/117 |
| 2006/0189842 A1 | * | 8/2006 | Hoeg ................... | A61B 1/0005 600/118 |
| 2007/0149846 A1 | * | 6/2007 | Chen .................. | A61B 1/00009 600/117 |
| 2007/0161853 A1 | | 7/2007 | Yagi et al. | |
| 2008/0071140 A1 | * | 3/2008 | Gattani ............... | A61B 1/0005 600/117 |

(Continued)

FOREIGN PATENT DOCUMENTS

| | | |
|---|---|---|
| EP | 2 700 351 A1 | 2/2014 |
| JP | H11-104072 A | 4/1999 |
| JP | 2001-046320 A | 2/2001 |
| JP | 2006-288869 A | 10/2006 |
| JP | 2009-297416 A | 12/2009 |
| JP | 2010-240000 A | 10/2010 |
| WO | 2005/077253 A1 | 8/2005 |
| WO | 2013/132880 A1 | 9/2013 |

OTHER PUBLICATIONS

Hakamata, Shinichi et al., "Reconstruction of 3D organ image using endoscope with Magneto-position-sensor", The Institute of Electronics, Information and Communication Engineers Technical Report, MI, Medical Imaging, Jun. 30, 2006, vol. 106, No. 145, pp. 13-18.

(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

An endoscope system includes: an insertion portion to be inserted into a predetermined luminal organ in a subject; an image pickup section provided in a vicinity of a distal end of the insertion portion, the image pickup section picking up an image of a predetermined range; an image pickup information acquiring section acquiring position information and gaze information about the image pickup section; a model image generating section generating a planar model image of the predetermined luminal organ; an image pasting processing section generating a pasted image obtained by pasting a subject image of an inside of the predetermined luminal organ onto the planar model image based on the position information and gaze information about the image pickup section; and an image pasting/presentation processing section presenting an image pickup range of the image pickup section on the pasted image based on the position information about the image pickup section.

11 Claims, 34 Drawing Sheets

(56) References Cited

U.S. PATENT DOCUMENTS

| | | | |
|---|---|---|---|
| 2008/0097150 A1* | 4/2008 | Hasegawa | A61B 1/0005 |
| | | | 600/109 |
| 2009/0036902 A1* | 2/2009 | DiMaio | A61B 34/10 |
| | | | 606/130 |
| 2009/0259102 A1* | 10/2009 | Koninckx | A61B 1/00181 |
| | | | 600/111 |
| 2011/0242301 A1* | 10/2011 | Morita | A61B 1/00009 |
| | | | 348/65 |
| 2012/0289825 A1* | 11/2012 | Rai | A61B 6/12 |
| | | | 600/425 |
| 2013/0027515 A1* | 1/2013 | Vinther | A61B 1/00177 |
| | | | 348/44 |
| 2014/0088357 A1 | 3/2014 | Ikuma et al. | |
| 2014/0236000 A1* | 8/2014 | Kozuka | A61M 25/09 |
| | | | 600/424 |
| 2014/0296644 A1* | 10/2014 | Zilberstein | A61B 1/06 |
| | | | 600/178 |
| 2016/0022125 A1* | 1/2016 | Nicolau | A61B 5/062 |
| | | | 600/424 |

OTHER PUBLICATIONS

International Search Report dated Jan. 13, 2015 issued in International Application No. PCT/JP2014/075099.

* cited by examiner

FIG. 15

| TIME | IMAGE | SENSOR INFORMATION | |
|---|---|---|---|
| | | POSITION | ROTATION |
| T1 | Img(1) | $(x_1, y_1, z_1)$ | $(\alpha_1, \beta_1, \gamma_1)$ |
| T2 | Img(2) | $(x_2, y_2, z_2)$ | $(\alpha_2, \beta_2, \gamma_2)$ |
| T3 | Img(3) | $(x_3, y_3, z_3)$ | $(\alpha_3, \beta_3, \gamma_3)$ |
| ⋮ | ⋮ | ⋮ | ⋮ |
| Tn | Img(n) | $(x_n, y_n, z_n)$ | $(\alpha_n, \beta_n, \gamma_n)$ |

ENDOSCOPE SYSTEM WITH IMAGE PASTING ON PLANAR MODEL

CROSS REFERENCE TO RELATED APPLICATION

This application is a continuation application of PCT/JP2014/075099 filed on Sep. 22, 2014 and claims benefit of Japanese Application No. 2013-201898 filed in Japan on Sep. 27, 2013, the entire contents of which are incorporated herein by this reference.

BACKGROUND OF THE INVENTION

1. Field of the Invention

The present invention relates to an endoscope system which presents an endoscopic image using a model image of an organ.

2. Description of the Related Art

Conventionally, endoscope systems have been widely used in medical and industrial fields. For example, in an endoscope system in the medical field, a surgeon inserts an insertion portion of an endoscope into a subject, and an endoscopic image obtained through an observation window provided at a distal end portion of the insertion portion is displayed on a display device. The surgeon can perform endoscopy, viewing the displayed endoscopic image. Furthermore, the endoscope system can record the endoscopic image. For example, a doctor uses a recorded endoscopic image of a lesioned part as a part of a medical record.

Further, a capsule endoscope system has been put to practical use recently. When a patient swallows the capsule endoscope, the capsule endoscope picks up an image of an inside of a body while moving inside of the body and records the image of the inside of the body.

In the case of the capsule endoscope, an enormous number of images are acquired. Therefore, a technique for extracting only images of an observation target site, such as a lesioned part, from among the acquired lot of images, and a technique for generating an image for diagnosis using an image having a high priority based on characteristic parameters when pasting a plurality of images onto a 3D model as disclosed in Japanese Patent Application Laid-Open Publication No. 2010-240000 as a first prior-art example have been proposed.

By the way, endoscopy may be performed again in order to observe a state of a lesioned part discovered in previous endoscopy, or the lesioned part discovered in the previous endoscopy may be treated with use of an endoscope.

Therefore, a doctor writes a position of a lesioned part discovered in examination in an examination target organ into a medical record. For example, when the examination target organ is a urinary bladder, the position of the lesioned part is specified by making a mark in a urinary bladder development diagram (schema) drawn in a medical record.

Further, in Japanese Patent Application Laid-Open Publication No. 2006-288869 as a second conventional example, it is disclosed that two-dimensional coordinate data of distal end portions of first to fourth endoscopes determined by a coordinate conversion operating section is inputted to an image representing circuit section, and the image representing circuit section displays video by each endoscope at a position on a monitor corresponding to a position of the endoscope, based on a plurality of pieces of video information obtained from the first to fourth endoscopes and position information obtained from a medical diagnosis image apparatus, that is, the two-dimensional coordinate data. Further, in this gazette, it is disclosed that video of a three-dimensional diseased part is displayed on the monitor as video in which the diseased part is planarly developed.

SUMMARY OF THE INVENTION

An endoscope system according to an aspect of the present invention is provided with: an insertion portion to be inserted into a predetermined luminal organ in a subject; an image pickup section provided in a vicinity of a distal end of the insertion portion, the image pickup section picking up an image of a predetermined range in the subject; an image pickup information acquiring section acquiring position information and gaze information about the image pickup section; a model image generating section generating a planar model image of the predetermined luminal organ; an image pasting processing section generating a pasted image obtained by pasting a subject image of an inside of the predetermined luminal organ onto the planar model image based on the position information and gaze information about the image pickup section; and an image pasting/presentation processing section presenting an image pickup range of the image pickup section on the pasted image generated by the image pasting processing section based on the position information about the image pickup section.

BRIEF DESCRIPTION OF THE DRAWINGS

FIG. 15 is a diagram showing an example of sensor information acquired in synchronization with images in a tabular form;

DETAILED DESCRIPTION OF THE PREFERRED EMBODIMENTS

An embodiment of the present invention will be described below with reference to drawings.

First Embodiment

Figure 1:
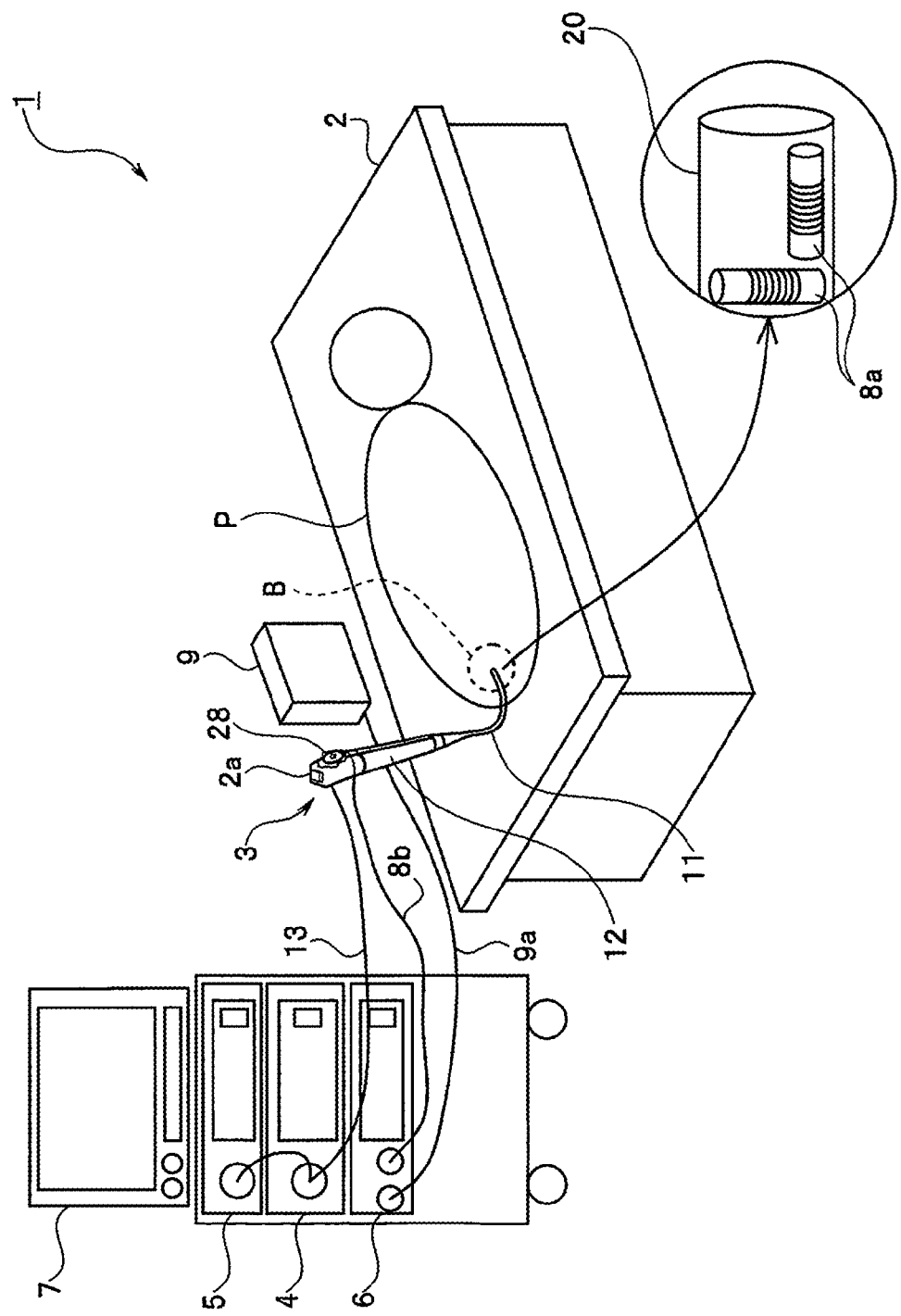
FIG. 1 is a perspective view showing a general configuration of an endoscope system of a first embodiment of the present invention.

As shown in FIG. 1, an endoscope system 1 of a first embodiment of the present invention has an endoscope 3 to be inserted into a patient P as a subject lying on a bed 2 for performing observation or examination; a light source apparatus 4 which supplies illuminating light to the endoscope 3; a processor 5 as a signal processing apparatus which performs signal processing for image pickup means of the endoscope 3; an image processing apparatus 6 which performs image processing, recording or the like for an image generated by the processor 5; a monitor 7 which displays an endoscopic image generated by the processor and an image for which image processing has been performed by the image processing apparatus 6; and a magnetic field generating apparatus 9 which detects a position of a magnetic sensor 8 provided near the image pickup means.

The endoscope 3 has an insertion portion 11 having flexibility, an operation portion 12 which is provided at a rear end (proximal end) of the insertion portion 11 and which is to be grasped by a surgeon to perform an operation such as bending, and a universal cable 13 extended from the operation portion 12.

Figure 2:
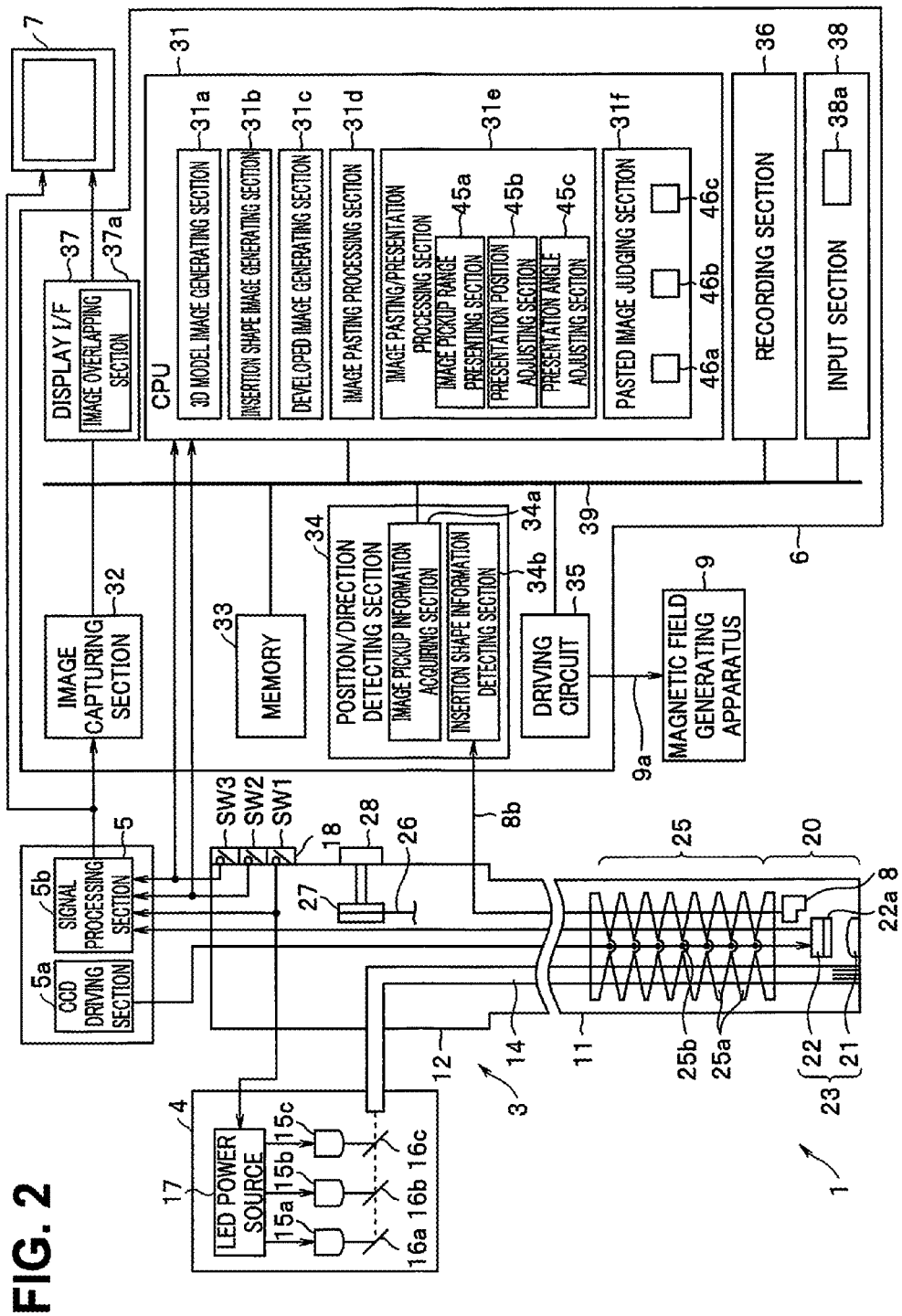
FIG. 2 is a block diagram showing a configuration of the endoscope system of the first embodiment of the present invention.

Further, as shown in FIG. 2, a light guide 14 which transmits illuminating light is inserted into the insertion portion 11. The light guide 14 extends through the universal cable 13 from the operation portion 12, and a light guide connector at an end portion of the light guide 14 is detachably connected with the light source apparatus 4.

As shown in FIG. 2, light emitting diodes (abbreviated as LEDs) 15*a*, 15*b*, and 15*c*, mirrors 16*a*, 16*b*, and 16*c* and an LED power source (circuit) 17 are provided in the light source apparatus 4. The LED 15*a* generates white light. The white light is reflected by the mirror 16*a* and, after that, transmitted through the dichroic mirrors 16*b*, 16*c* and caused to be incident on the end portion of the light guide 14.

Further, the LEDs 15b and 15c generate narrow band blue light (Bn) and green light (Gn) the center wavelengths of which are set in a vicinity of 415 nm and in a vicinity of 540 nm, respectively. The narrow band light Bn by the LED 15b is transmitted through the dichroic mirror 16c and caused to be incident on the end portion of the light guide 14 after being selectively reflected by the dichroic mirror 16b. Further, the narrow band light Gn by the LED 15c is caused to be incident on a hand-side end portion of the light guide 14 after being selectively reflected by the dichroic mirror 16c.

The operation portion 12 of the endoscope 3 is provided with a scope switch 18 provided with a switching switch SW1 for performing an operation for, between a normal light observation mode (also referred to as a white light observation mode or a WBI mode) and a narrow band light observation mode (also referred to as an NBI mode), switching from one observation mode to the other observation mode, a release switch SW2 for performing a release operation, a freeze switch SW3 for performing a freeze operation and the like.

When the surgeon grasping the operation portion 12 of the endoscope 3 operates the switching switch SW1, a switching signal is sent to the light source apparatus 4 and the processor 5, and the LED power source 17 of the light source apparatus 4 switches light emission between the LED 16a and the LEDs 16b, 16c according to the switching signal. Further, the processor 5 performs signal processing corresponding to the switching signal.

Further, a release signal in a case of operating the release switch SW2 is inputted to a central processing unit (abbreviated as a CPU) 31 constituting control means in the image processing apparatus 6, and the CPU 31 performs a control operation for recording an endoscopic image.

Note that it is also conceivable that an operation signal in the case of operating the release switch SW2 is inputted to (the signal processing section 5b in) the processor 5, the processor 5 generates a release signal from the operation signal and sends the release signal to the CPU 31 of the image processing apparatus 6, and the CPU 31 performs a control operation for recording an endoscopic image by the release signal inputted from the processor 5. FIG. 2 shows a configuration example in which a release signal is inputted to the processor 5 and the CPU 31.

Further, a freeze signal in a case of operating the freeze switch SW3 is inputted to (the signal processing section 5b in) the processor 5, and the processor 5 performs a process for converting a movie endoscopic image to a still image. Further, the freeze signal is also sent to the CPU 31, and the CPU 31 grasps that a freeze operation has been performed.

Illuminating light caused to be incident on the hand-side end portion of the light guide 14 is transmitted to a distal end face of the light guide 14 by the light guide 14. The distal end face of the light guide 14 is arranged at an illuminating window provided at a distal end portion 20 of the insertion portion 11, and the illuminating light is emitted to an outside from the illuminating window. In the present embodiment, since the insertion portion 11 is inserted into a urinary bladder B as a predetermined organ via a urethra of the patient P, illuminating light illuminates an inside of the urinary bladder B.

As shown in FIG. 2, an objective lens 21, and a charge coupled device (abbreviated as a CCD) 22 arranged at an image forming position of the objective lens 21 are arranged at the distal end portion 20 of the insertion portion 11. An image pickup section (or image pickup unit) 23 constituting the image pickup means for picking up an image of an inside of the predetermined organ is formed by the objective lens 21 and the CCD 22. The image pickup section 23 picks up an image of a site illuminated by illuminating light and outputs an image pickup signal as an electrical signal obtained by photoelectric conversion.

Note that the CCD 22 is provided with a mosaic filter 22a which performs color separation, for example, into wavelength bands of red (R), green (G) and blue (B) for each pixel. Therefore, for example, in a case of the normal light observation mode (WBI mode), the CCD 22 outputs broad band R, G and B signals obtained by color separation by the mosaic filter 22a, and, in a case of the NBI mode, by image pickup under the illuminating light of the LEDs 15b, and 15c, the CCD 22 outputs narrow band G and B signals (abbreviated as Gn and Bn signals) obtained by color separation by the mosaic filter 22a.

The processor 5 has a CCD driving section (or CCD driving circuit) 5a and applies a CCD driving signal generated by the CCD driving section 5a to the CCD 22 via a signal line 24 inserted through the endoscope 3. By the application, the CCD 22 outputs an image pickup signal obtained by photoelectric conversion to a signal processing section (or signal processing circuit) 5b provided in the processor 5 via the signal line 24 inserted through the endoscope 3.

The signal processing section 5b generates a video signal (image signal) to for displaying (an image picked up by the CCD 22) as an endoscopic image to be displayed on the monitor 7. Since the insertion portion 11 is inserted into the urinary bladder B as shown in FIG. 1 also, an image signal corresponding to an image picked up in the urinary bladder B is generated. The movie image signal generated by the signal processing section 5b is outputted to the monitor 7, and the monitor 7 displays an endoscopic image (also referred to as a picked-up image or a real image) corresponding to the movie image signal.

The monitor 7 has a PinP (picture in picture) function and displays a developed image as a plane model image (obtained by planarly developing a three-dimensional model image corresponding to the urinary bladder B which is to be described later) and an image of an insertion shape of a distal end side of the insertion portion 11, together with the endoscopic image.

Note that it is also conceivable to input an endoscopic image to the image processing apparatus 6 without utilizing the PinP function of the monitor 7, and provide image overlapping means for overlapping the endoscopic image with a developed image and an insertion shape image in the image processing apparatus 6.

Figure 8:
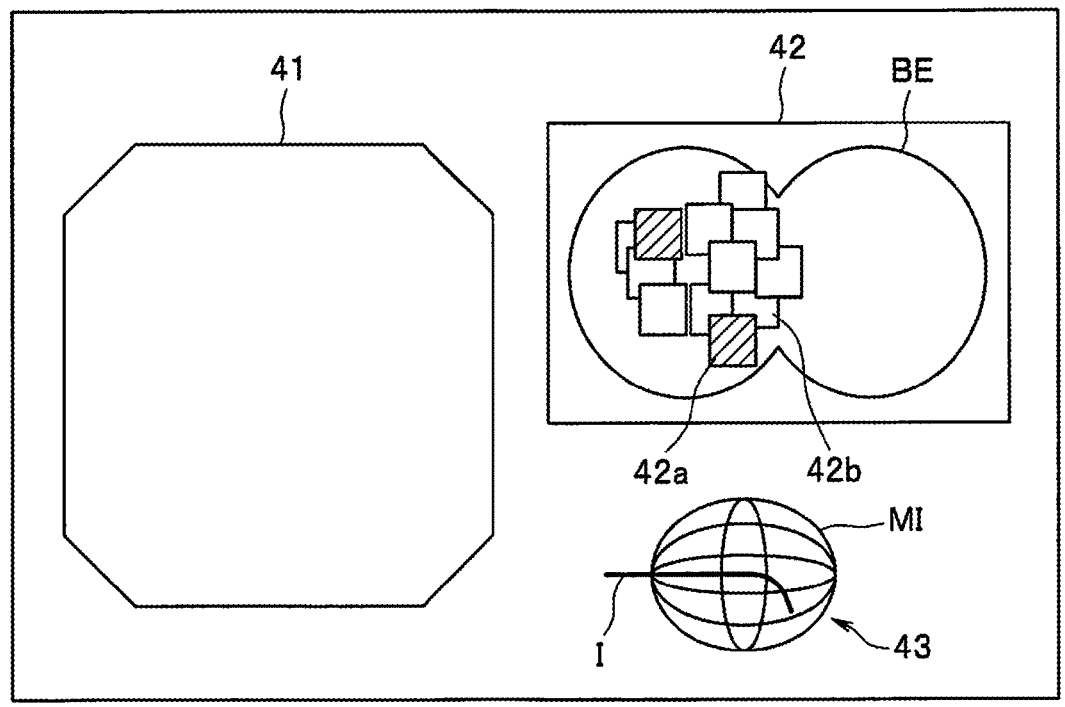
FIG. 8 is a diagram showing display areas for three images displayed on a monitor.

For example, it is also conceivable to temporarily store an endoscopic image generated by the signal processing section 5b in the processor 5 into, for example, a first predetermined area of a first frame memory (not shown) in a memory 33 in the image processing apparatus 6, temporarily store a developed image into a second predetermined area of a second frame memory, temporarily store an insertion shape image into a third predetermined area of a third frame memory, overlap the three images read simultaneously from the three frame memories on a display interface (abbreviated as a display I/F) 37, and output an overlap image signal to the monitor 7. In this case, the display I/F 37 has a function of an image overlapping section 37a (as shown in FIG. 1). It is possible to display mainly three images on a display surface of the monitor 7 by PinP or the function of the image overlapping section 37a of the monitor 7 as shown in FIG. 8.

Further, in the present embodiment, in order that a three-dimensional position of the image pickup section 23 arranged at the distal end portion 20 of the insertion portion 11 and a gaze direction of the image pickup section 23 can be detected, the magnetic sensor 8 configured with two magnetic coils 8a constituting two position sensors is arranged at a position near the CCD 22 at the distal end portion 20 as shown in FIG. 1.

As shown in FIG. 2, the magnetic sensor 8 is connected to a position/direction detecting section (or position/direction detecting circuit) 34 in the image processing apparatus 6 via a signal line 8b inserted through the endoscope 3. The position/direction detecting section 34 calculates the position and gaze direction of the image pickup section 23 by detecting three-dimensional positions of the two magnetic coils 8a.

More specifically, the position/direction detecting section 34 controls a driving circuit 35 which drives the magnetic field generating apparatus 9 to apply a driving signal for generation of a magnetic field, to the magnetic field generating apparatus 9 via a signal line 9a from the driving circuit 35 so as to cause the magnetic field generating apparatus 9 to generate a predetermined magnetic field, detects the magnetic field by the two the magnetic coils 8a, and generates, from a detection signal of the detected magnetic field, three-dimensional positions of the two magnetic coils 8a, three-dimensional position coordinates (x, y, z) of the image pickup section 23 near the three-dimensional positions of the two magnetic coils 8a and data of the gaze direction of the image pickup section 23 (that is, an Euler angle ($\psi$, $\theta$, $\phi$)), that is, position/direction information in real time.

Thus, the position/direction detecting section 34 has a function of an image pickup information acquiring section (or image pickup information acquiring circuit) 34a as image pickup information acquiring means for acquiring position information and direction information from the magnetic sensor 8 and detecting position information and gaze information about the image pickup section 23 as the image pickup means.

Note that, since the magnetic sensor 8 is provided at the distal end portion 20, the position/direction detecting section 34 has a function of calculating a position (information) and a gaze direction (information) of the image pickup section 23 as well as a function of calculating a position (information) and a (longitudinal) direction (information) of the distal end portion 20. Therefore, an expression that the position/direction detecting section 34 calculates (detects) a position and direction of the distal end portion 20 is also used. Note that it will be described later that the magnetic sensor 8 constituting the image pickup information acquiring means is provided in a member connected to the image pickup means.

In the present embodiment, positions and directions of the distal end portion 20 calculated by the position/direction detecting section 34 are stored in a time series manner.

For example, the memory 33 stores the calculated positions and directions of the distal end portion 20 in a time series manner, and the position/direction detecting section 34 calculates an insertion shape (mainly on the distal end side) of the insertion portion 11 inserted into the urinary bladder B by calculating a current position and direction of the distal end portion 20 referring to past information stored in the memory 33 in a time series manner Therefore, the position/direction detecting section 34 has a function of an insertion shape information detecting section (or insertion shape information detecting circuit) 34b constituting insertion shape information detecting means for detecting insertion shape information in the case of the insertion portion 11 being inserted into the urinary bladder B as the predetermined organ. Note that a configuration is also conceivable in which the image pickup information acquiring section 34a is provided with the function of the insertion shape information detecting section 34b.

As shown in FIG. 2, the insertion portion 11 is provided with a bending portion 25 on a hand-side end portion of the distal end portion 20, the bending portion 25 being provided with bending pieces 25a capable of freely bending in upward and downward directions and in right and left directions. Note that, though FIG. 2 shows an example in which rivets 25b enabling a bend, for example, only in the upward and downward directions are provided for simplification, the rivets 25b are actually provided so as to enable a free bend in the upward and downward directions and the right and left directions alternately.

Further, a wire 26 is inserted through the insertion portion 11, the wire 26 causing the bending pieces 25a to bend in the upward and downward directions and the right and left directions individually by being pulled. A distal end of the wire 26 is fixed to a distal end member constituting the distal end portion 20 (not shown), and a rear end of the wire 26 is coiled around a pulley 27 arranged in the operation portion 12. The surgeon can bend the bending portion 25 in any direction among the upward, downward, right and left directions by performing an operation of turning a bending knob 28 coupled with the pulley 27. By causing the bending portion 25 to bend, an image pickup direction of the image pickup section 23 provided at a distal end of the bending portion 25 can be changed. As described later, it is possible to, by bending the bending portion 25 much, observe (pick up an image of) an inner wall surface on a cervix RP side which is an entrance side of insertion into the urinary bladder B.

As shown in FIG. 2, the image processing apparatus 6 has the CPU 31 which forms control means for controlling an operation of each section in the image processing apparatus 6, an image capturing section (or image capturing circuit) 32 which captures an image signal outputted from the processor 5, the memory 33 which temporarily stores an image signal inputted via the image capturing section 32 and temporarily stores various kinds of information, and the position/direction detecting section 34 which detects the position and gaze direction of the image pickup section 23 arranged at the distal end portion 20 from a detection signal of the magnetic sensor 8.

Further, the image processing apparatus 6 has the driving circuit 35 which drives the magnetic field generating apparatus 9, a recording section (storage section) 36 which records (or stores) an endoscopic image by a release signal, the display interface (display I/F) 37 which displays an endoscopic image and the like on the monitor 7 and an input section (or user I/F) 38 which inputs various kinds of data, and the CPU 31, the image capturing section 32, the memory 33, the position/direction detecting section 34, the recording section (storage section) 36, the display I/F 37, the input section 38 are mutually connected via a data bus 39.

Various kinds of processing programs to be executed by the CPU 31 and various kinds of data including data of the urinary bladder B as the predetermined organ into which the insertion portion 11 is to be inserted are stored in the recording section 36, and the CPU 31 generates a three-dimensional model (3D model) image M1 of the urinary bladder B into which the distal end portion 20 of the insertion portion 11 is inserted. Therefore, the CPU 31 has a function of a 3D model image generating section (or 3D model image generating circuit) 31*a* which generates the 3D model image M1 of the urinary bladder B as the predetermined organ.

Further, when the distal end side of the insertion portion 11 is inserted into the urinary bladder B, the CPU 31 generates an overlap image so that an insertion shape of the distal end side of the insertion portion 11 is displayed on the 3D model image M1, based on information about a position and direction of the distal end portion 20 by the position/direction detecting section 34. Therefore, the CPU 31 has a function of an insertion shape image generating section (or insertion shape image generating circuit) 31*b* which generates an insertion shape image I in the case of the distal end side of the insertion portion 11 being inserted into the urinary bladder B (as an overlap image on a 3D model image).

Further, the CPU 31 has a function of a developed image generating section (or developed image generating circuit) 31*c* which generates a plane model image obtained by planarly developing a 3D inner surface of the urinary bladder B on the 3D model image M1 using a two-dimensional (2D) model obtained by cutting the urinary bladder B by a predetermined plane which includes the cervix RP (see FIG. 3) to be an entrance from the urethra into the urinary bladder B and developing the urinary bladder B into two circles.

Further, the CPU 31 has an image pasting processing section (or image pasting processing circuit) 31*d* which, for an endoscopic image picked up by the image pickup section 23 (which may be abbreviated simply as an image), performs a process for pasting an image conforming to a predetermined condition onto a developed image, and an image pasting/presentation processing section (or image pasting/presentation processing circuit) 31*e* which performs a process for presenting the image pasted on the developed image by the monitor 7 as display means. By referring to an image generated by the image pasting/presentation processing section 31*e* and pasted on a developed image BE on the monitor 7, the surgeon can easily grasp a site the image of which is being picked up in the urinary bladder B.

Note that, actually, in the case of pasting an (endoscopic) image conforming to (or satisfying) the predetermined condition onto a developed image, a corresponding position on the inner surface on the 3D model image M1 is determined, the position is projected onto a 2D model image M2, and then the image is pasted at the projected position. Alternatively, an image pasted at the corresponding position on the inner surface on the 3D model image M1 may be projected to the 2D model image M2 to obtain a pasted image.

Further, when a release operation is performed by the surgeon, the CPU 31 records an endoscopic image from the processor 5 to the recording section 36. That is, the recording section 36 configured with a memory or the like forms an image recording section which records an endoscopic image.

Figure 3:
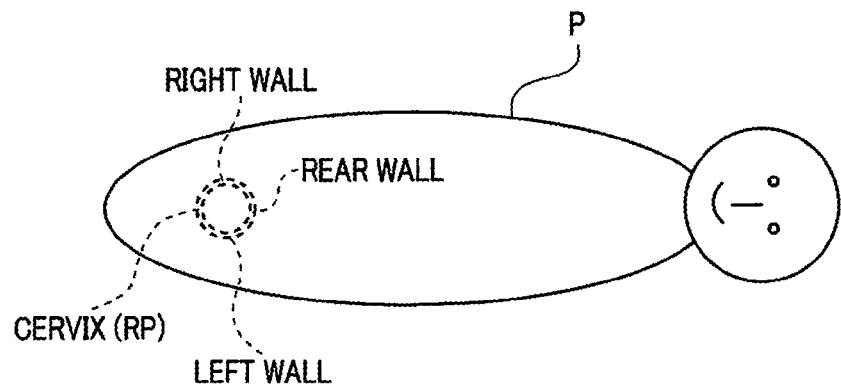
FIG. 3 is a diagram schematically showing positions and names of a urinary bladder as a predetermined organ to be an observation target in a patient.
Figure 4:
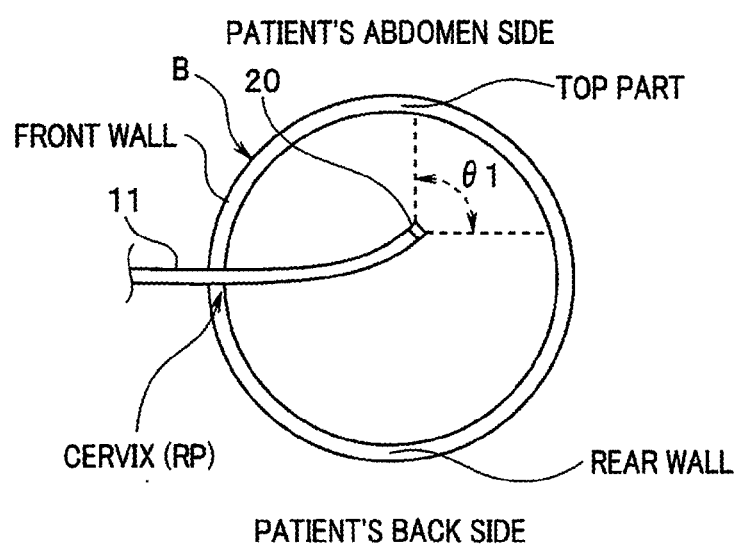
FIG. 4 is a diagram showing each part of the urinary bladder in a case where an insertion portion of an endoscope is inserted into the urinary bladder.

FIG. 3 schematically shows the urinary bladder B of the patient P for whom endoscopy is to be performed in a state of the insertion portion 11 being inserted in the urinary bladder B in the present embodiment, and FIG. 4 shows the 3D model image M1 obtained by modeling the urinary bladder B, together with an insertion shape image.

The urinary bladder B is separated into a plurality of areas, that is, the cervix RP to be an opening end portion on a distal end side (on a depth side) of the urethra and to be the entrance to the urinary bladder B, a top part on an abdomen side, a rear wall from a back to a position facing the cervix RP, a right wall on a right side when seen from the patient P, and a left wall on a left side when seen from the patient P. Examination of the urinary bladder B is performed in a state that the patient P lies on his back and in a state that the urinary bladder B is filled with predetermined liquid.

When the distal end side of the insertion portion 11 is inserted into the urinary bladder B, the distal end side of the insertion portion 11 in a case of using the 3D model image M1 is as shown in FIG. 4. In FIG. 4, an observation field by the image pickup section 23 in the urinary bladder B is indicated by θ1.

Figure 5:
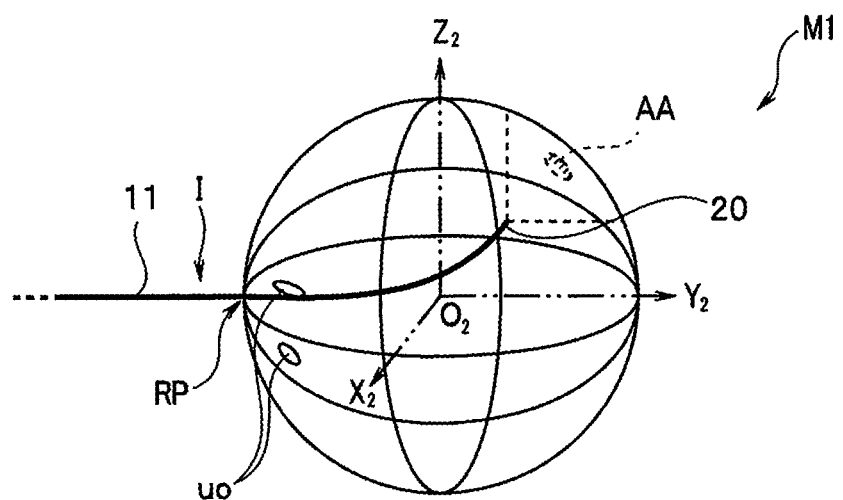
FIG. 5 is a diagram showing an insertion shape image of the insertion portion together with a 3D model image obtained by modeling the urinary bladder.

Further, the insertion shape information detecting section 34*b* calculates (detects) an insertion shape on the distal end side of the insertion portion 11 in the urinary bladder B based on position/direction information by the position/direction detecting section 34, and the insertion shape image generating section 31*b* generates the insertion shape image I so that an image obtained by overlapping the insertion shape image I on the 3D model image M1 can be displayed on the monitor 7 as shown in FIG. 5.

Figure 6:
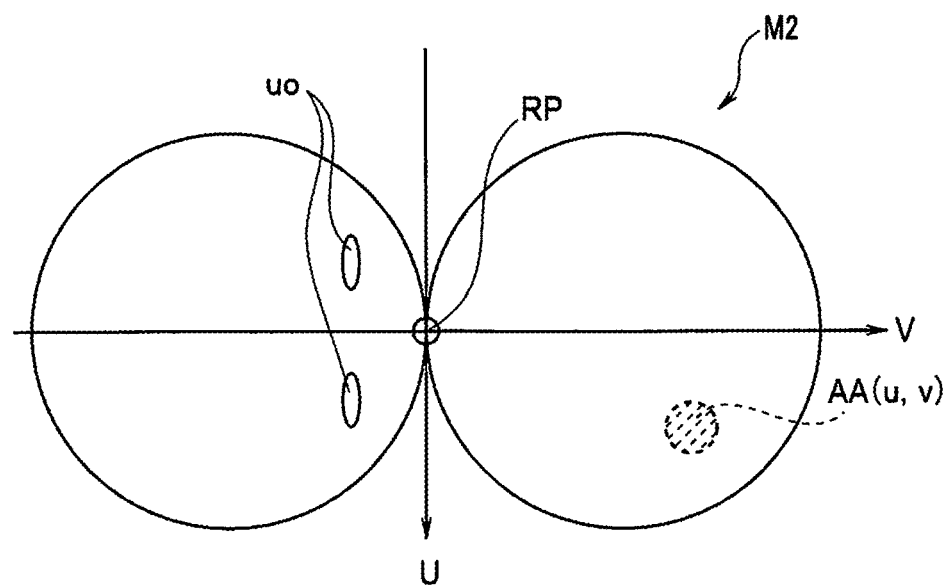
FIG. 6 is a diagram showing a 2D model showing the urinary bladder planarly.
Figure 7:
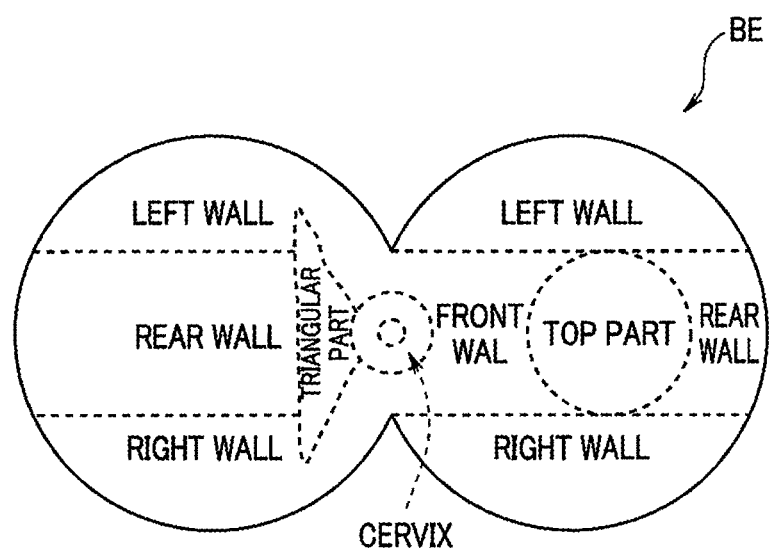
FIG. 7 is a diagram showing a plane model image obtained by planarly developing and modeling an inner surface of the urinary bladder and a position of each part in the urinary bladder.

Further, the CPU 31 divides the 3D model image M1 shown in FIG. 5 by a plane passing through the cervix RP, more specifically, a plane which includes $X_2$-$Y_2$ in FIG. 5 to generate a 2D model image M2 as shown in FIG. 6. Furthermore, in consideration of a size of the cervix RP from the 2D model image M2 in FIG. 6, the developed image generating section 31*c* of the CPU 31 generates a 2D developed image (hereinafter referred to simply as a developed image) BE as a 2D model image of the urinary bladder B as shown in FIG. 7 (obtained by varying FIG. 6). Note that two ureteral orifices of the urinary bladder B exist at positions indicated by uo in FIGS. 5 and 6. Further, for example, when a lesioned part AA exists in the urinary bladder B at a position indicated by dotted lines in FIG. 5, the position of the lesioned part AA in FIG. 5 corresponds to a position indicated by dotted lines in FIG. 6.

FIG. 7 shows an arrangement example of, in a case of observing respective portions in the urinary bladder B in a standard observation state, areas of the respective portions projected on the developed image BE.

If judging that a picked-up image picked up by the image pickup section 23 (or an endoscopic image at a predetermined timing) conforms to the predetermined condition, the image pasting processing section 31*d* of the CPU 31 pastes the picked-up image at a corresponding position on the developed image BE as a pasted image. In this case, the image pasting processing section 31*d* refers to information about a position and direction of the position/direction detecting section 34 to paste the pasting target picked-up image.

Further, in the case of pasting the picked-up image on the developed image BE as a pasted image, for example, a size of the pasted image may be adjusted according to relative magnitudes of sizes of the developed image BE and the picked-up image.

In the present embodiment, for example, the image pasting processing section 31*d* performs adjustment of the size of a picked-up image, such as reduction, to paste the picked-up image as a pasted image at a central position corresponding to the picked-up image (picked up by the image pickup section 23) on a developed image BE. However, it is possible to select performing pasting in a manner that a range of the picked-up image substantially corresponds to an area on the developed image BE. The pasted image is referred to as a same-magnification pasted image (or a first pasted image).

Therefore, the image processing apparatus 6 is provided with a view angle information acquiring section which, in advance, acquires view angle information deciding an image pickup range of the image pickup section 23 in the endoscope 3 which is actually inserted into the urinary bladder B. If the endoscope 3 is provided with identification information (ID), the view angle information may be acquired based on the identification information. If the endoscope 3 is not provided with the identification information (ID), the view angle information may be inputted from the input section 38 or the like and acquired and stored into the memory 33, the recording section 36 or the like so that the view angle information can be referred to when required. Further, the image pickup information acquiring section 34a may have a function of acquiring the information about the view angle of the image pickup section 23.

In such a case, if image pickup is performed by the image pickup section 23 with a large view angle or in a state where a distance from a wall surface of the urinary bladder B is long, one same-magnification pasted image occupies a large area on a developed image BE. Therefore, there is a possibility that, after such pasting is performed, an arrangement state of the respective portions on the developed image BE is difficult to recognize.

Therefore, it is also conceivable to, after an appropriate time period elapses after a same-magnification pasted image is pasted as described above, cause the same-magnification to be a reduced pasted image obtained by reducing the size of the same-magnification pasted image to one severalth without changing the central position.

As for the appropriate time period described above, for example, if a time period shorter than a time period before pasting a next picked-up image is set, it is possible to substantially prevent lowering of a function of, at the time of pasting the next picked-up image, grasping which area on the developed image BE the picked-up image was taken for. That is, the image pasting processing section 31d constituting image pasting/presenting means may be adapted to, when pasting a next picked-up image after pasting a picked-up image picked up by the image pickup means on a developed image BE as a planar model image, at a corresponding position on the planar model image, as a first pasted image in a manner that the picked up image substantially corresponds to an area corresponding to the picked-up image, change the first pasted image to a pasted image reduced (to one severalth or the like) (see FIG. 22A).

Alternatively, when a process for pasting the next picked-up image starts or when the process for pasting the next picked-up image is decided, a same-magnification pasted image may be changed to a reduced pasted image and presented.

Further, it is also possible to paste a reduced pasted image as a pasted image from the beginning so that a picked-up image can be pasted on a developed image BE and presented according to the surgeon's preference. Further, it is also conceivable to paste a picked-up image when a distance between the distal end portion 20 (or the image pickup section 23) and the inner wall surface of the urinary bladder B is within an appropriate range.

FIG. 8 shows an example of a developed image BE on which a pasted image 42a is pasted and an insertion shape image I using a 3D model image M1 which are displayed on the monitor 7 together with an endoscopic image.

Further, the surgeon can select a presentation position at the time of pasting a pasted image onto a developed image BE and presenting (displaying) the pasted image, and a size, a presentation angle and the like in the case of presentation, from the input section 38 configured with a keyboard and the like.

Therefore, the input section 38 has a function of a presentation selecting section (or presentation selecting device) 38a for selecting a presentation method, content of presentation and the like at the time of presenting (displaying) a pasted image.

As shown in FIG. 8, an endoscopic image (a picked-up image) is displayed in a first area 41 as an endoscopic image display area (or a real image display area or a picked-up image display area) on a left side of a display screen; a developed image BE on which a pasted image 42a is pasted is displayed in a second area 42 as a developed image display area at an upper part on a right side; and an insertion portion shape image I obtained by overlapping a form of the insertion portion 11 on a 3D model image M1 is displayed in a third area 43 as an insertion shape display area on a lower side of the second area.

In the present embodiment, the image pasting/presentation processing section 31e is provided with a function of an image pickup range presenting section (or image pickup range presenting device) 45a as image pickup range presenting means for presenting an image pickup range (image pickup area) on a developed image BE corresponding to an image pickup range (area) for which image pickup is currently being performed by the image pickup section 23 on a developed image BE so that an observation position for which an image is currently being picked up is easily recognized as described later, based on position/direction (or gaze) information about the image pickup section 23; and a function of a presentation position adjusting section (or presentation position adjusting device) 45b which adjusts a presentation position by dividing and moving a developed image BE, or the like so that a pasted image 42a in a case of displaying a picked-up image being observed as the pasted image 42a is located at a center of the developed image BE.

Further, the image pasting/presentation processing section 31e has a function of a presentation angle adjusting section (or presentation angle adjusting device) 45c which adjusts an orientation of a pasted image 42a displayed on a developed image BE so as to make it easy to grasp a correspondence relationship between an endoscopic image and the pasted image 42a because, when the bending portion 25 is bent, upward, downward, right and left directions at a time of the endoscopic image as an observed image being displayed in the first area 41 on the monitor 7 as described later change.

Note that the adjustment is not limited to the case of changing the orientation of a pasted image 42a on a developed image BE as a planar model image, but it is also conceivable to make it easy to grasp a relationship between both images by changing an angle indicating an orientation of the whole developed image BE.

Further, the CPU 31 has a function of a pasted image judging section (or pasted image judging circuit) 31f which judges whether an image picked up by the image pickup section 23 conforms to the predetermined condition or not. In the present embodiment, an image judged to conform to the predetermined condition by the pasted image judging section 31f is pasted by the image pasting processing section 31d, and an image judged not to conform to the predetermined condition becomes an image which is not pasted by the image pasting processing section 31d.

In the present embodiment, the pasted image judging section 31f has an image processing judging section (or image processing judging circuit) 46a which makes the judgment about whether the predetermined condition is conformed to or not by image processing, a position/direction information judging section 46b which makes the judgment by position/direction information as sensor information, and an information-such-as-distance judging section (or information-such-as-distance judging circuit) 46c which makes the judgment by information about the distance from the distal end portion 20 to the urinary bladder wall and information about a gaze direction.

Further, when a pasted image 42a is already pasted on a developed image BE, the image pasting processing section 31d performs a pasting process so as to paste a newest pasted image on the old pasted image 42b. In this case, the newest pasted image 42a is pasted in a state that the newest pasted image 42a does not overlap with the old pasted image 42b existing outside a size of the newest image at a position where the newest pasted image 42a is to be pasted.

Further, the CPU 31 has a function of an insertion-into-urinary-bladder judging section which detects (judges) insertion into the urinary bladder by monitoring, for example, an amount of change in luminance of an endoscopic image (picked-up image) inputted from the processor 5 via the image capturing section 32 and utilizing change in the luminance at a time when the distal end portion 20 of the insertion portion 11 enters the inside of the urinary bladder B from a urethra.

More specifically, when the distal end portion 20 of the insertion portion 11 enters the inside of the urinary bladder B from the urethra, it is judged that the distal end portion 20 has entered the inside of the urinary bladder B if a luminance value changes from a high state to a low state. Note that it is also conceivable to judge more certainly that the distal end portion 20 has entered the inside of the urinary bladder B by monitoring a color tone of the endoscopic image, an amount of change in texture of the endoscopic image and the like in addition to luminance. Further, it is also conceivable to attach a position detecting sensor such as a magnetic sensor not shown at a predetermined position near the urinary bladder to make it possible to three-dimensionally detect a position of the entrance to the urinary bladder from a position detection result of the position detecting sensor. Note that, though the 3D model image generating section 31a, the insertion shape image generating section 31b, the developed image generating section 31c, the image pasting processing section 31d, the image pasting/presentation processing section 31e and the pasted image judging section 31f are configured with the CPU 31 in FIG. 2, the case where they are configured with the CPU 31 is not limited to this, and it is also conceivable to make a configuration using a dedicated electronic circuit, an FPGA and the like.

The endoscope system 1 of the present embodiment is provided with: the endoscope 3 whose insertion portion 11 is inserted into the urinary bladder B as a predetermined organ in a subject; the image pickup section 23 provided in the endoscope 3 as the image pickup means for picking up an inside of the predetermined organ in the subject; the position/direction detecting section 34 provided on a member connected in a vicinity of or to the image pickup means as the image pickup information acquiring means for detecting position information and gaze information (gaze direction information) about the image pickup means; the developed image generating section 31c as developed image generating means for generating a developed image BE as a planar model image obtained by planarly developing a model image corresponding to the predetermined organ; and the image pasting/presentation processing section 31e as the image pasting/presentation means for pasting an image of the inside of the predetermined organ based on the position information about the image pickup means onto the planar model image generated by the developed image generating means and changing a method for presenting the planar model image or content of presentation based on the position information.

Figure 9:
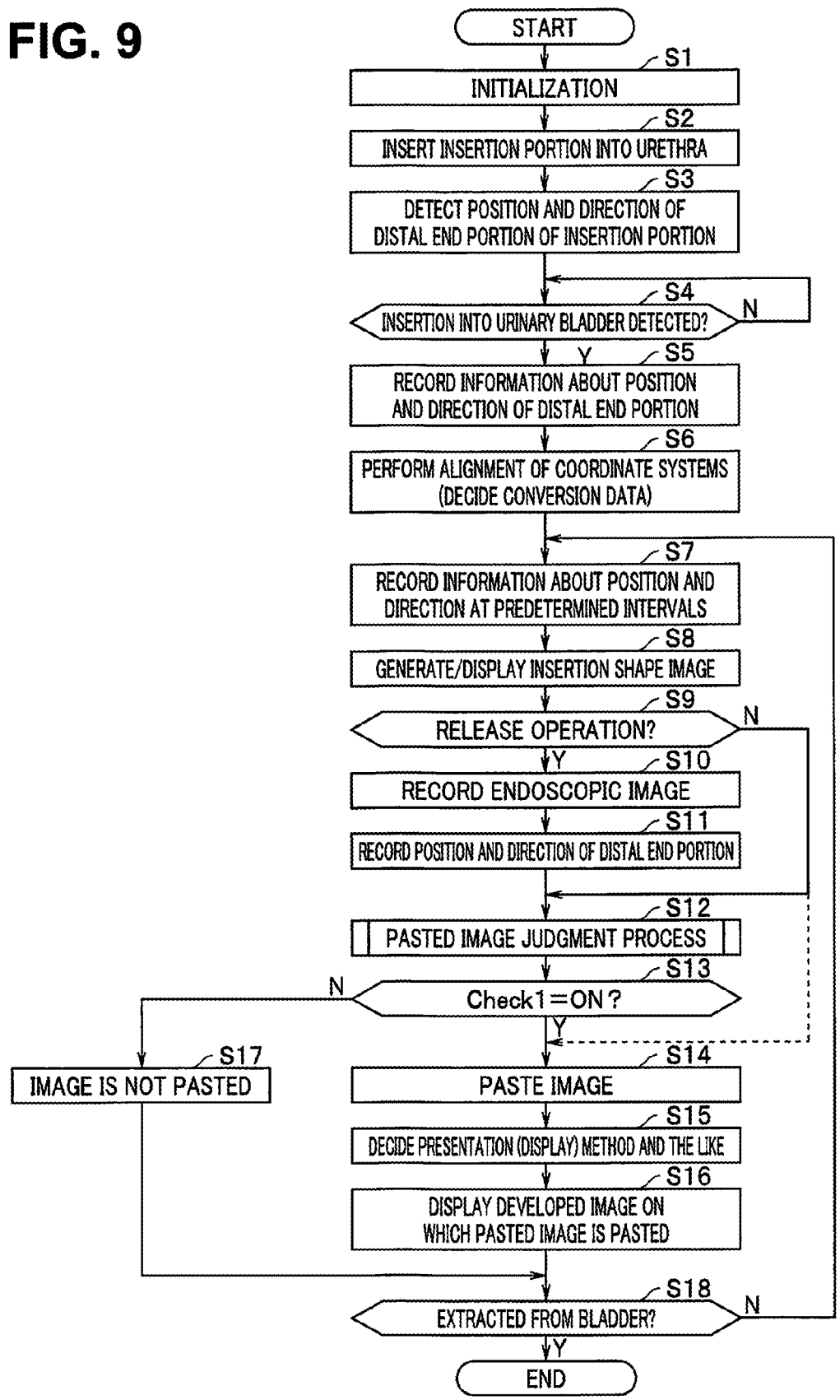
FIG. 9 is a flowchart showing an example of general content of a process in a case of observing an inside of the urinary bladder in the first embodiment.

Next, an operation of the present embodiment will be described. FIG. 9 shows an example of general content of the operation of the present embodiment.

When the endoscope system 1 is powered on, the light source apparatus 4, the processor 5, the image processing apparatus 6, the monitor 7 and the like enter an operating state, and the surgeon performs initialization at first step S1. When the surgeon gives an input instruction to perform endoscopy for the inside of the urinary bladder B by the endoscope 3 from the input section 38 in the initialization, the CPU 31 reads data of the urinary bladder B. Then, the three areas 41, 42, and 43 to be displayed on the monitor 7 are prepared in the monitor 7. After initialization ends, the surgeon inserts the insertion portion 11 of the endoscope 3 from the urethra of the patient P at next step S2.

Further, as shown at step S3, the position/direction detecting section 34 detects a position and direction of the image pickup section 23 at the distal end portion 20 of the insertion portion 11 using a first coordinate system $(X_0 Y_0 Z_0)$ on a basis of the magnetic field generating apparatus 9, from a detection signal of the magnetic sensor 8.

Further, as shown at step S4, the insertion-into-urinary-bladder judging section of the CPU 31 monitors an endoscopic image generated by the processor 5, makes a judgment (detection) about whether the distal end portion 20 of the insertion portion 11 has been inserted into the urinary bladder (the entrance to the inside of the urinary bladder, that is, the cervix RP) and continues the process until the distal end portion 20 is inserted into the urinary bladder B.

When insertion of the distal end portion 20 into the urinary bladder B is detected, the CPU 31 performs control so that information about a position and direction of the distal end portion 20 is recorded to the recording section 36 as shown at step S5. Further, as shown at step S6, the CPU 31 performs alignment (including directions) for enabling conversion between first coordinate system (X0Y0Z0) by the magnetic field generating apparatus 9, and a second coordinate system (X2Y2Z2) of the 3D model image M1 in FIG. 5 and an intermediate coordinate system (X1Y1Z1) of the 2D model image M2 in FIG. 6 at a three-dimensional position of the cervix RP as the entrance to the urinary bladder B where the distal end portion 20 is located.

That is, in order to make it possible to identify an arbitrary position in one coordinate system, in other coordinate systems also, with the position of the entrance to the urinary bladder B as a known reference position in each coordinate system, alignment among the respective coordinate systems is performed (or a process for deciding conversion data required for performing conversion among the coordinate systems is performed) (equations (4) to (23) to be described later). By the alignment, it becomes possible for the distal end portion 20 of the insertion portion 11 to identify an arbitrary position and direction in the urinary bladder B using any of the first, intermediate and second coordinate systems.

After the process of step S6, the CPU 31 manages the position and direction of the distal end portion 20 mainly by the intermediate and second coordinate systems.

As shown at step S7, the CPU 31 acquires information about the position and direction of the distal end portion 20, for example, every predetermined time, and performs control so that the acquired position and direction information is recorded to the recording section 36. Further, as shown at step S8, (the insertion shape image generating section 31c of) the CPU 31 refers to immediately previous information about the position and direction of the distal end portion 20 recorded in the recording section 36 to generate an insertion shape image I of the distal end side of the insertion portion 11 in the urinary bladder, and displays the insertion shape image I at a corresponding coordinate position on the 3D model image M1. FIG. 5 shows an example of the case.

Further, FIG. 5 shows that the image pickup section 23 provided at the distal end portion 20 of the insertion portion 11 picks up an endoscopic image in the urinary bladder B, for example, with a view angle of θ1. Further, when a lesioned part AA exists at a position indicated by dotted lines, the position of the lesioned part AA in the coordinate system of FIG. 5 corresponds to a position indicated by dotted lines in (the coordinate system of) the 2D model image M2 in FIG. 6.

As shown at step S9, the CPU 31 monitors a release operation. Then, when a release operation is performed, the CPU 31 records an endoscopic image at a timing when the release operation was performed to the recording section 36 as shown at step S10. Further, as shown at step S11, the CPU 31 records information about a position and direction of the distal end portion 20 at the time of acquiring the endoscopic image to be recorded, to the recording section 36 in association with the endoscopic image. Note that, if the release operation is not performed in the process of step S9, the flow proceeds to a process of step S12. The flow may be adapted to proceed to a process of step S14 as indicated by a dotted line.

Further, as shown at step S12, the pasted image judging section 31f of the CPU 31 performs a process for judgment about whether or not the endoscopic image conforms to a pasting condition set in advance. Then, the pasted image judging section 31f sets a sign corresponding to a result of the judgment about whether the endoscopic image conforms to the pasting condition or not. The pasted image judging section 31f sets, for example, Check1 as the sign corresponding to the judgment result to ON if judging that the endoscopic image conforms to the pasting condition, and sets, for example, Check1 to OFF if judging that the endoscopic image does not conform to the pasting condition.

As shown at step S13, the image pasting processing section 31d of the CPU 31 judges whether or not the judgment result shows that the endoscopic image conforms to the pasting condition (more specifically, Check1 is ON). Then, if the judgment result shows that the endoscopic image conforms to the pasting condition, the image pasting processing section 31d performs a process for pasting the endoscopic image as shown at step S14.

Further, as shown at step S15, the image pasting/presentation processing section 31e performs a process for deciding a presentation method and the like in a case of pasting the endoscopic image onto a developed image BE by the image pasting processing section 31d based on the information about the position and direction of the distal end portion 20 and displaying (presenting) the endoscopic image with the monitor 7. As shown at next step S16, the image pasting processing section 31d outputs the developed image BE where the pasted image for which the presentation method and the like has been decided is pasted, to the monitor 7 via the display I/F 37. Then, on the monitor 7, a pasted image 42a which has been processed by the image pasting/presentation processing section 31e is displayed in a state of being pasted at a corresponding position on the developed image BE.

On the other hand, if a judgment result shows that the endoscopic image does not conform to the pasting condition in the process at step S13, the image pasting processing section 31d does not perform the process for pasting the endoscopic image (picked-up image) as shown at step S17. After the process of S16 or S17, the CPU 31 judges whether or not the insertion portion 11 has been extracted (pulled out) from the urinary bladder, from detection information of the position/direction detecting section 34 as shown at step S18.

If a judgment result shows that the insertion portion 11 has not been extracted from the urinary bladder, the flow returns to the process of step S7, and the process from steps S7 to S18 is repeatedly performed. On the other hand, if a judgment result shows that the insertion portion 11 has been extracted from the urinary bladder, the CPU 31 ends the process of FIG. 9.

Figure 10:
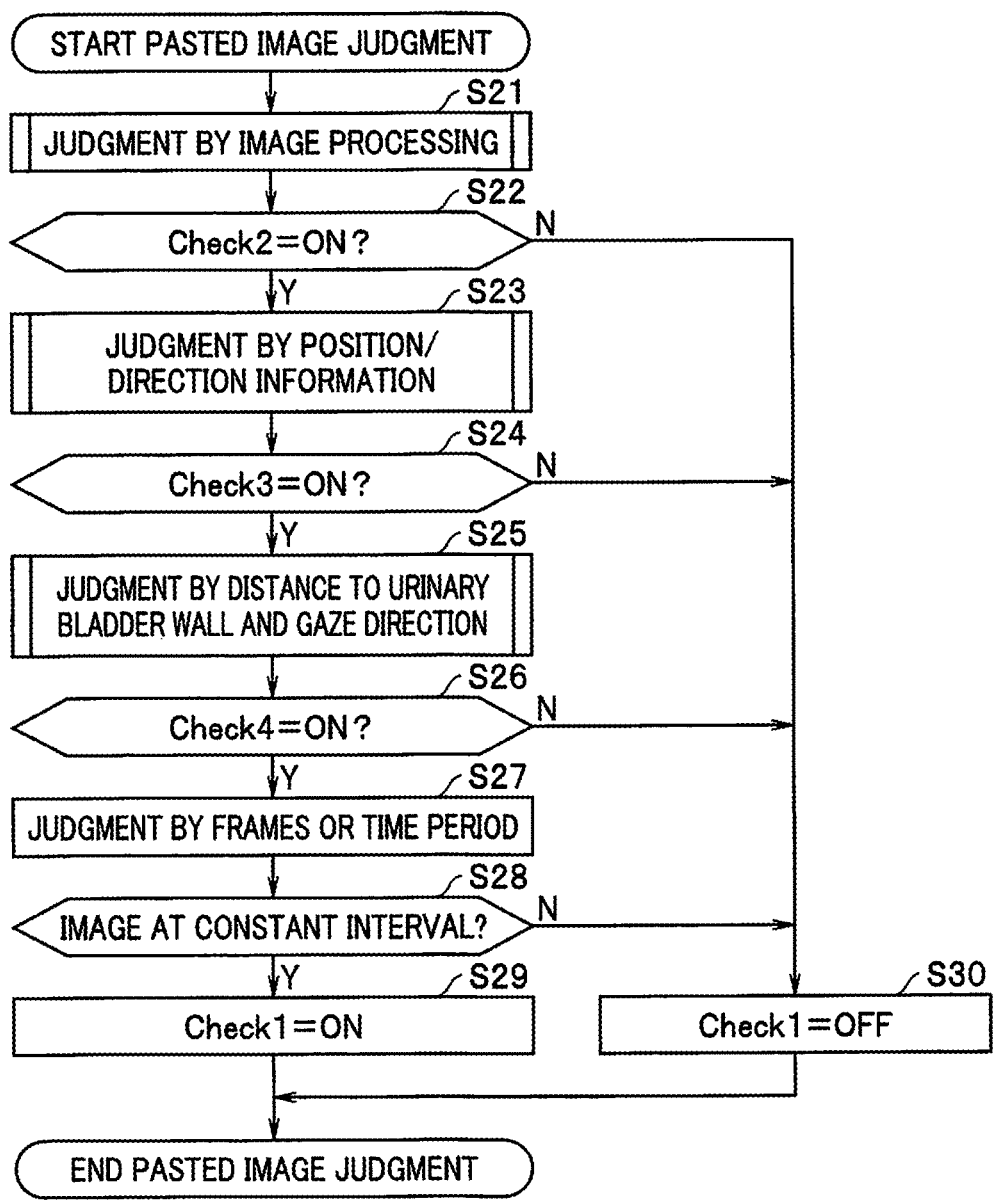
FIG. 10 is a flowchart showing details of a pasted image judgment process in FIG. 9.

Next, a part of content of the process in FIG. 9 will be described in more detail. FIG. 10 shows details of the process of step S12 in FIG. 9.

Figure 12:
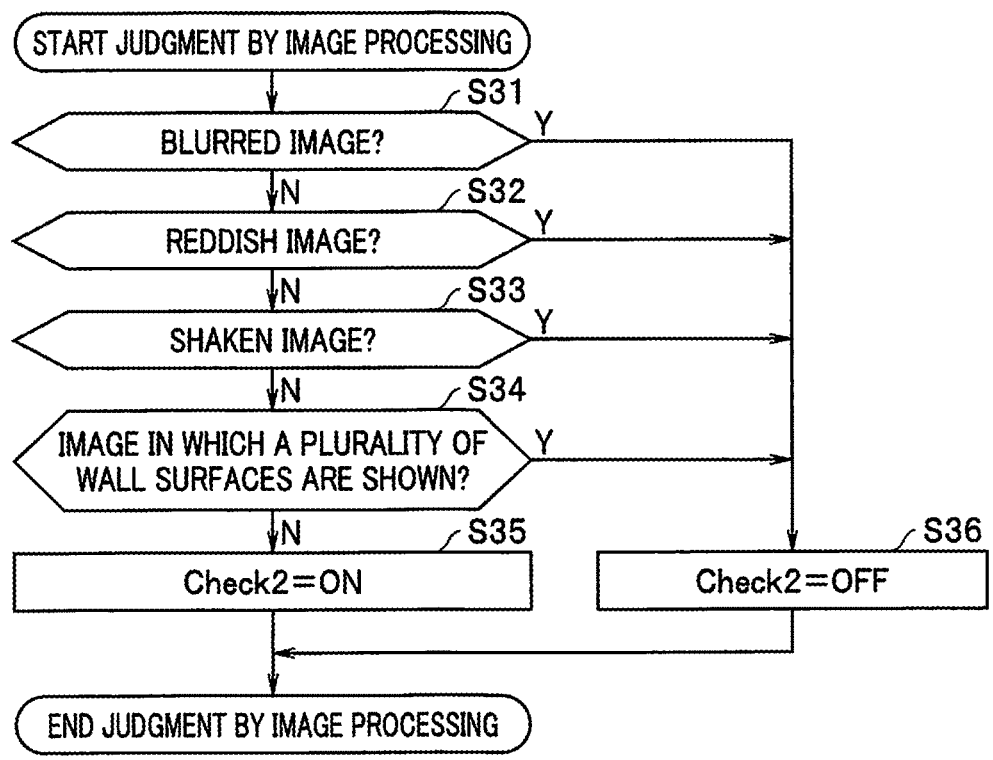
FIG. 12 is a flowchart showing details of a judgment process by image processing in FIG. 10.

When the pasted image judgment process starts in FIG. 10, (the image processing judging section or image processing judging circuit 46a of) the pasted image judging section 31f of the CPU 31 performs image processing for a processing target endoscopic image (at step S12 in FIG. 9) and makes a judgment about whether the endoscopic image conforms to the pasting condition or not by a result of the image processing at first step S21 as shown in FIG. 12. The image processing judging section 46a sets, for example, Check2 to ON if judging that the endoscopic image conforms to the pasting condition as a result of judgment by the image processing, and sets, for example, Check2 to OFF if judging that the endoscopic image does not conform to the pasting condition.

As shown at next step S22 in FIG. 10, the pasted image judging section 31f judges whether Check2 as a judgment result is ON or not. If Check2 is ON, the position/direction information judging section (or position/direction information judging circuit) 46b of the pasted image judging section 31f makes a judgment about whether the processing target endoscopic image conforms to the pasting condition using position/direction information based on the sensor 8 as shown at next step S23. The position/direction information judging section 46b sets, for example, Check3 to ON if judging that the endoscopic image conforms to the pasting condition, and sets, for example, Check3 to OFF if judging that the endoscopic image does not conform to the pasting condition.

As shown at next step S24, the pasted image judging section 31f judges whether Check3 as a judgment result is ON or not. If Check3 is ON, the information-such-as-distance judging section (or information-such-as-distance judging circuit) 46c makes a judgment about whether the processing target endoscopic image conforms to the pasting condition or not using the distance from (the image pickup section 23 at) the distal end portion 20 to the urinary bladder wall and gaze information as shown at next step S25.

The information-such-as-distance judging section 46c sets, for example, Check4 to ON if judging that the endoscopic image conforms to the pasting condition, and sets, for example, Check4 to OFF if judging that the endoscopic image does not conform to the pasting condition.

As shown at next step S26, the pasted image judging section 31f judges whether Check4 as the judgment result is ON or not. If Check4 is ON, the pasted image judging section 31f performs a judgment process by frames or a time period as shown at next step S27. Then, at next step S28, the pasted image judging section 31f makes a judgment about whether or not the endoscopic image is an endoscopic image after a constant interval of the number of frames or after elapse of a constant time period from an endoscopic image adopted for previous pasting. If the endoscopic image conforms to the condition, the pasted image judging section 31f causes Check1 to be ON as a judgment result that the processing target endoscopic image conforms to the pasting condition, at next step S29.

Figure 11:
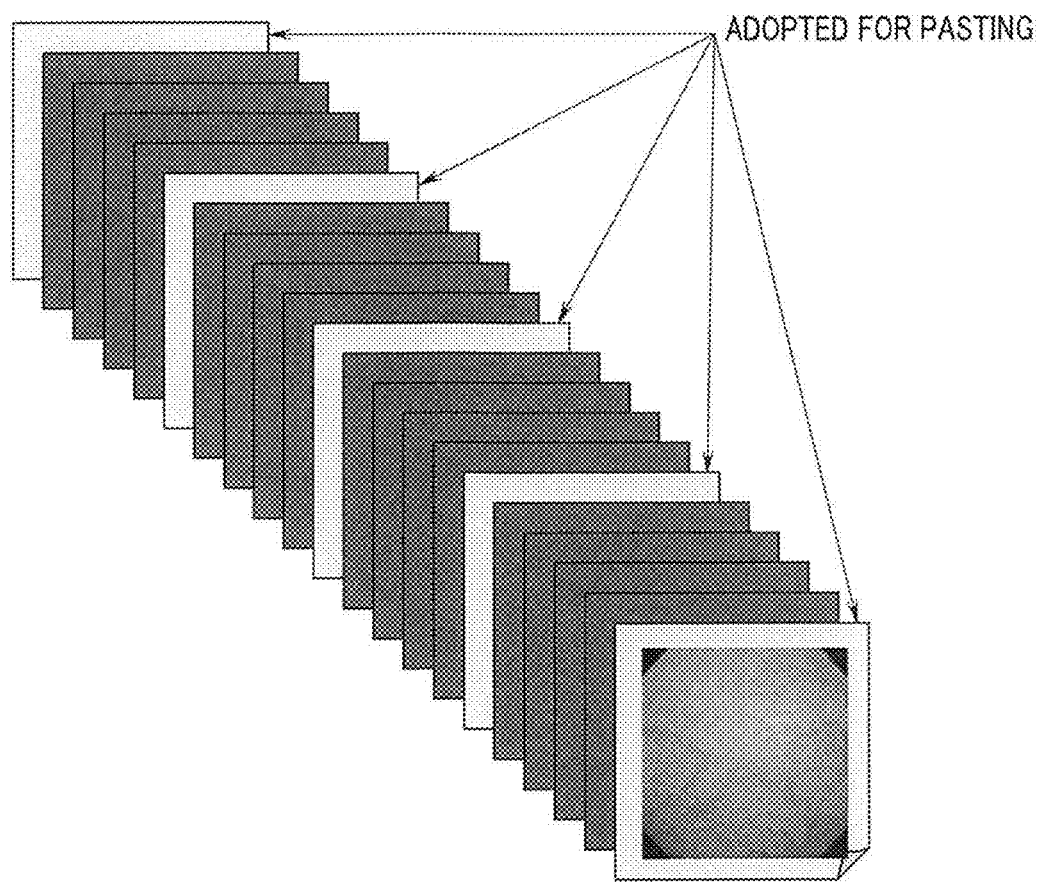
FIG. 11 is an explanatory diagram of a case of adopting endoscopic images acquired every constant number of frames or every constant time period as pasted images.

FIG. 11 shows an example of an endoscopic image conforming to the pasting condition in the judgment process of step S29. As shown in FIG. 11, it is judged that only endoscopic images at constant intervals (more specifically, at intervals of five frames) conform to the pasting condition.

On the other hand, if Check2 is not ON at step S22 in FIG. 10, if Check3 is not ON at step S24, if Check4 is not ON at step S26, or if the endoscopic image does not conform to the condition of step S28, then the pasted image judging section 31f causes Check1 to be OFF as a judgment result that the processing target endoscopic image does not conform to the pasting condition, at step S30, and ends the process of FIG. 10.

FIG. 12 shows details of the judgment process by image processing at step S21 in FIG. 10. When the judgment by image processing starts, the image processing judging section 46a of the pasted image judging section 31f makes a judgment about whether the processing target endoscopic image is a blurred image or not, at first step S31.

Figure 13A:
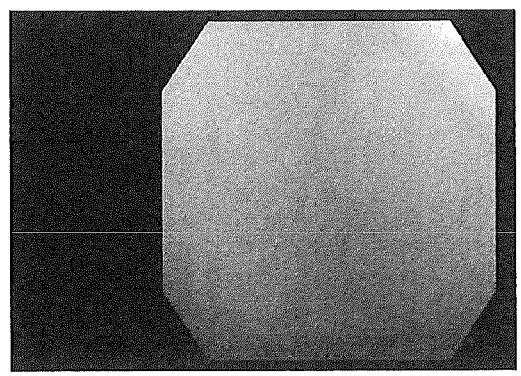
FIGS. 13A to 13D are diagrams showing examples of a blurred image and the like related to the process by FIG. 12.

Whether the endoscopic image is a blurred image or not can be judged based on whether or not more edge components than a threshold are detected in the endoscopic image. FIG. 13A shows an example of a blurred image.

Figure 13B:
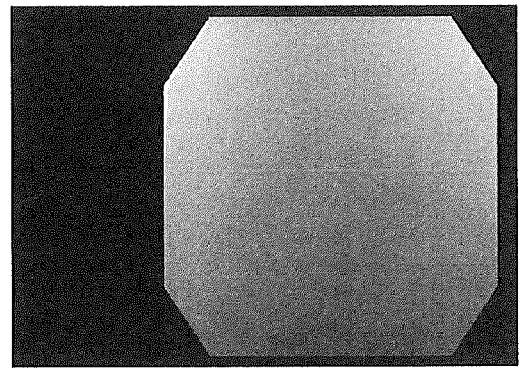

If the endoscopic image is not a blurred image, the image processing judging section 46a judges whether the endoscopic image is a reddish image or not at next step S32. Whether the endoscopic image is a reddish image or not can be judged based on pixel values of R pixels in the endoscopic image. FIG. 13B shows an example of a reddish image the whole of which has a reddish tone.

Figure 13C:
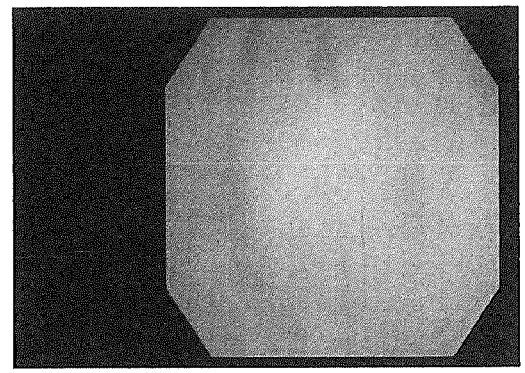

If the endoscopic image is not a reddish image, the image processing judging section 46a judges whether the endoscopic image is a camera-shaken image or not at next step S33. Whether the endoscopic image is a camera-shaken image or not can be judged based on edge components in the endoscopic image. FIG. 13C shows an example of a longitudinally camera-shaken image. Note that step S31 and step S33 may be performed together.

Figure 13D:

If the endoscopic image is not a camera-shaken image, the image processing judging section 46a judges whether or not the endoscopic image is such an image that a plurality of walls (surfaces) are shown in the endoscopic image at the next step S34. As for whether or not the endoscopic image is an image in which a plurality of walls (surfaces) are shown, whether or not a belt-shaped or linear image with a low luminance runs can be judged based on edge components in the endoscopic image. FIG. 13D shows an example of an image in which a plurality of walls (surfaces) are shown with steps.

If the endoscopic image is not such an image that a plurality of walls (surfaces) are shown in the endoscopic image, the image processing judging section 46a causes Check2 to be ON as the judgment result that the endoscopic image conforms to the pasting condition by condition processing by image processing at next step S35. On the other hand, if judging that the endoscopic image is a blurred image, a reddish image, a camera-shaken image or an image in which a lot of wall surfaces are shown through the judgment processes of steps S31 to S34, the image processing judging section 46a sets Check2 to OFF as the judgment result that the endoscopic image does not conform to the pasting condition. Then, the image processing judging section 46a ends the process in FIG. 12.

Figure 14:
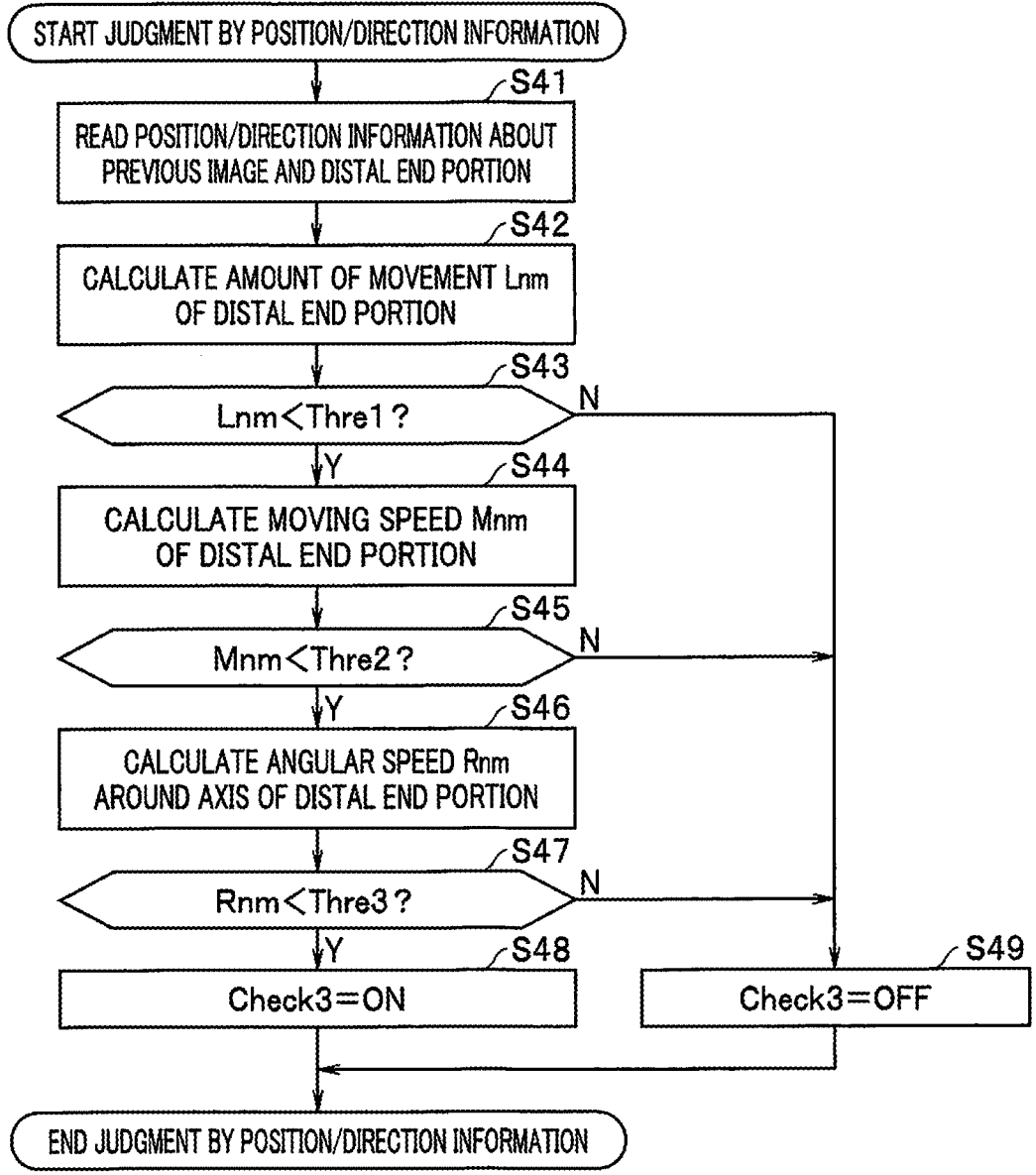
FIG. 14 is a flowchart showing details of a judgment process using position/direction information in FIG. 10.

FIG. 14 shows details of the judgment process by position/direction information at step S23 in FIG. 10. When the judgment starts, the position/direction information judging section 46b (of the pasted image judging section 31f) reads from the position/direction detecting section 34 position/direction information about an endoscopic image before an endoscopic image currently acquired (abbreviated as a previous image), at first step S41.

When a newest p-th endoscopic image to be a processing target, at step S12 in FIG. 9 or in FIGS. 13A to 13D is indicated by Img(p), position/direction information about an endoscopic image Img(p−1) acquired in a (p−1)th turn, which is one frame before the p-th endoscopic image, is also read. Then, as described below, for the two p-th and (p−1)th endoscopic images, or two n-th and m-th endoscopic images expressed more generally, an amount of movement Lnm is calculated by an equation (1) below.

$$Lnm = ((x_n - x_m)^2 + (y_n - y_m)^2 + (z_n - z_m)^2)^{1/2} \quad (1)$$

In the equation (1), $x_n$, $y_n$, $z_n$ and $x_m$, $y_m$, $z_m$ are position information about the distal end portion 20 and the image pickup section 23, respectively, in the three-dimensional coordinate system $(X_2 Y_2 Z_2)$. Therefore, the amount of Lnm can be said to indicate an amount of movement of the distal end portion 20 and can be also said to indicate an amount of movement of an endoscopic image acquired by the image pickup section 23. For example, an amount of movement between the p-th and (p−1)th endoscopic images picked up by the image pickup section 23 is calculated on an assumption of n=p and m=p−1; and an amount of movement between the p-th and (p−2)th endoscopic images on an assumption of n=p and m=p−2. Further, an amount of movement between the (p+1)th and (p−1)th endoscopic images may be calculated on an assumption of n=p+1 and m=p−1.

At next step S43, the position/direction information judging section 46b judges whether or not the amount of movement Lnm is smaller than an amount-movement threshold Thre1.

If a judgment result shows that the amount of movement Lnm is smaller than the amount-movement threshold Thre1 at step S43, the position/direction information judging section 46b calculates a moving speed Mnm of the distal end portion 20 by an equation (2) below at next step S44.

$$Mnm = ((x_n - x_m)^2 + (y_n - y_m)^2 + (z_n - z_m)^2)^{1/2} / (T_n - T_m) \quad (2)$$

In the equation (2), $T_n$ and $T_m$ indicate time at which an endoscopic image Img(n) is acquired and time at which an endoscopic image Img(m) is acquired, respectively (here, n>m). For example, a moving speed of the p-th endoscopic image Img(p) by the image pickup section 23 is calculated on the assumption of n=p and m=p−1; and a moving speed of the (p−1)th endoscopic image Img(p−1) by the image pickup section 23 on the assumption of n=p and m=P−2. Further, the moving speed of the p-th endoscopic image Img(p) by the image pickup section 23 may be calculated on the assumption of n=p+1 and m=p−1.

At next step S45, the position/direction information judging section 46b judges whether or not the moving speed Mnm is smaller than a moving-speed threshold Thre2.

If a judgment result shows that the moving speed Mnm is smaller than the threshold Thre2 at step S45, the position/direction information judging section 46b calculates an angular speed Rnm as a rotation speed around a longitudinal axis of the distal end portion 20 by an equation (3) below at next step S46.

$$Rnm=|\delta_n-\delta_m|/(T_n-T_m) \quad (3)$$

In the equation (3), $\delta_n$ and $\delta_m$ are angles around the longitudinal axis of the distal end portion 20 in the three-dimensional coordinate system ($X_2Y_2Z_2$), respectively.

At next step S47, the position/direction information judging section 46b makes a judgment about whether or not the calculated angular speed Rnm is smaller than an angular speed threshold Thre3. If a judgment result shows that the angular speed Rnm is smaller than the threshold Thre3, the position/direction information judging section 46b causes Check3 to be ON as the judgment result that the endoscopic image conforms to the pasting condition by the condition processing by position/direction information, at next step S48.

On the other hand, if it is judged that the amount of movement Lnm, the moving speed Mnm and the angular speed Rnm are equal to or larger than the threshold Thre1, Thre2 and Thre3, respectively, in the judgment processes of steps S43, S45 and 47, the position/direction information judging section 46b sets Check3 to OFF as the judgment result that the endoscopic image does not conform to the pasting condition, at step S49. Then, the position/direction information judging section 46b ends the process of FIG. 14.

Note that, as shown in FIG. 15, the position/direction detecting section 34 acquires or calculates information about a position ($x_i$, $y_i$, $z_i$) of the distal end portion and a rotation angle ($\alpha_i$, $\beta_i$, $\gamma_i$) corresponding to an Euler angle, from sensor information acquired by the two magnetic coils 8a in synchronization with time Ti (i=1, 2, . . . , n) at which an endoscopic image (also simply referred to an image) of each frame is acquired (picked up) by the image pickup section 23. Then, as described in FIG. 14, the position/direction information judging section 46b calculates the amount of movement Lnm, the moving speed Mnm and the angular speed Rnm and judges whether or not they are smaller than the thresholds, respectively.

Figure 16A:
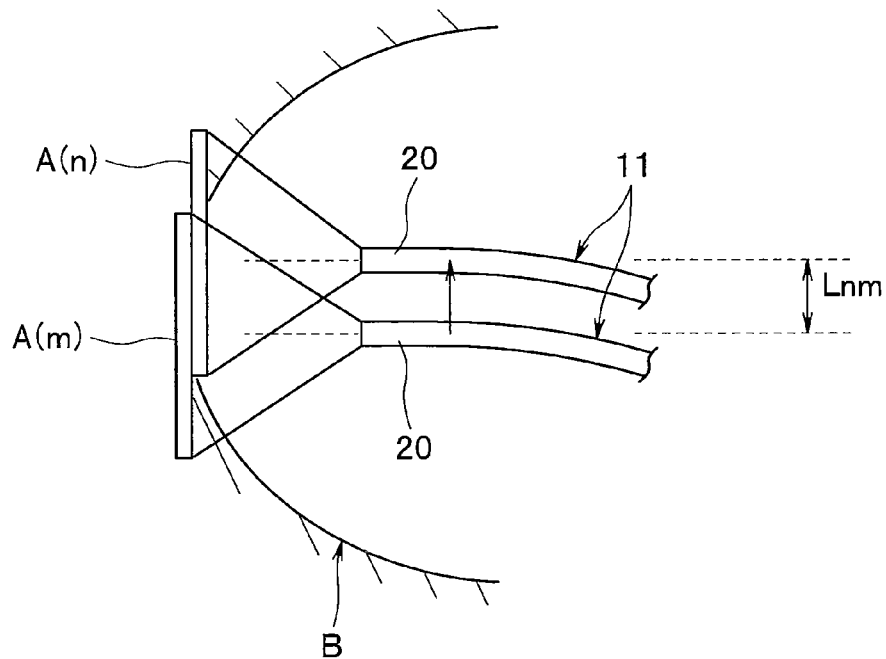
FIGS. 16A and 16B are explanatory diagrams for judgment by an amount of movement and for a moving speed in FIG. 14.

FIG. 16A shows a state of (the image pickup section 23 in) the distal end portion 20 of the insertion portion 11 acquiring endoscopic images Img(m) and Img(n) of the m-th and n-th frames for the inner surface of the urinary bladder. Note that target areas A(m) and A(n) the images of which are schematically picked up in FIG. 16A correspond to the endoscopic images Img(m) and Img(n), respectively. Then, if the amount of movement Lnm is smaller than the threshold Thre1, the endoscopic image is adopted as a pasted image, and, if the amount of movement Lnm is equal to or larger than the threshold Thre1, the endoscopic image is not adopted as a pasted image.

Figure 16B:
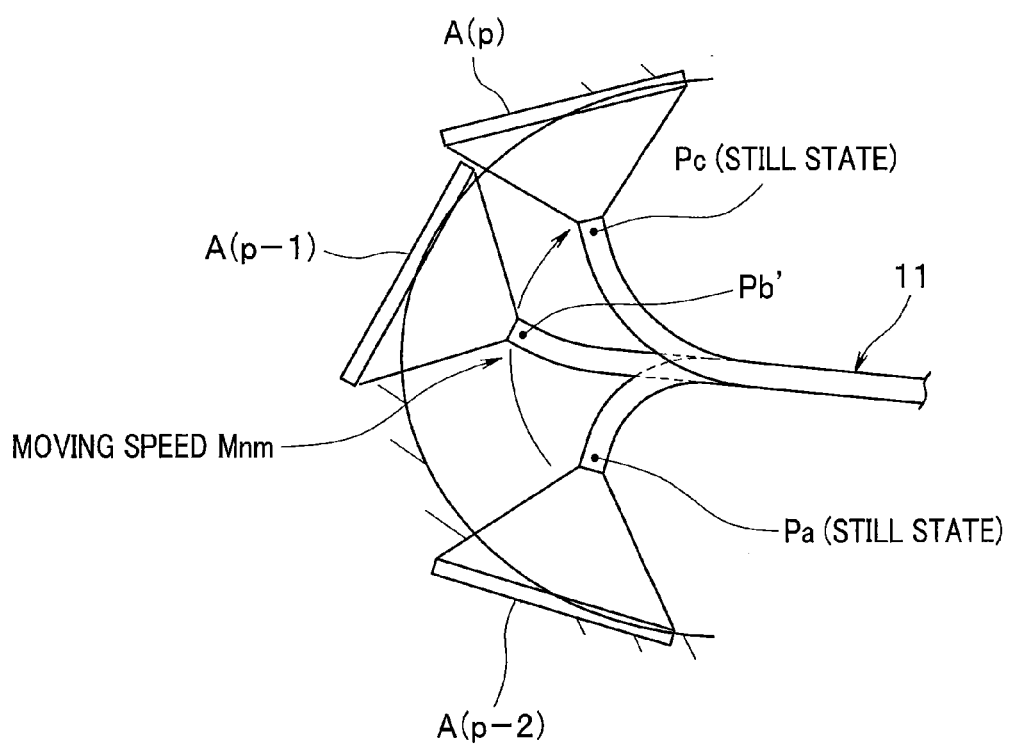

Further, FIG. 16B shows an example of an explanatory diagram of the moving speed. At positions Pa, Pc in a still state, the distal end portion 20 (the image pickup section 23 in the distal end portion) picks up images of target areas A(p-2), A(p) corresponding to endoscopic images Img(p-2) and Img(p). Further, the image pickup section 23 in the distal end portion performs image pickup at a position Pb' between the positions Pa and Pc while moving and picks up an image of a target area A(p-1).

In such a case, since the moving speed Mnm at the position Pb' is equal to or larger than the threshold Thre2, there is a strong possibility that a camera-shaken image is obtained. Such an image is judged to be an image not to be used for pasting.

Figure 17:
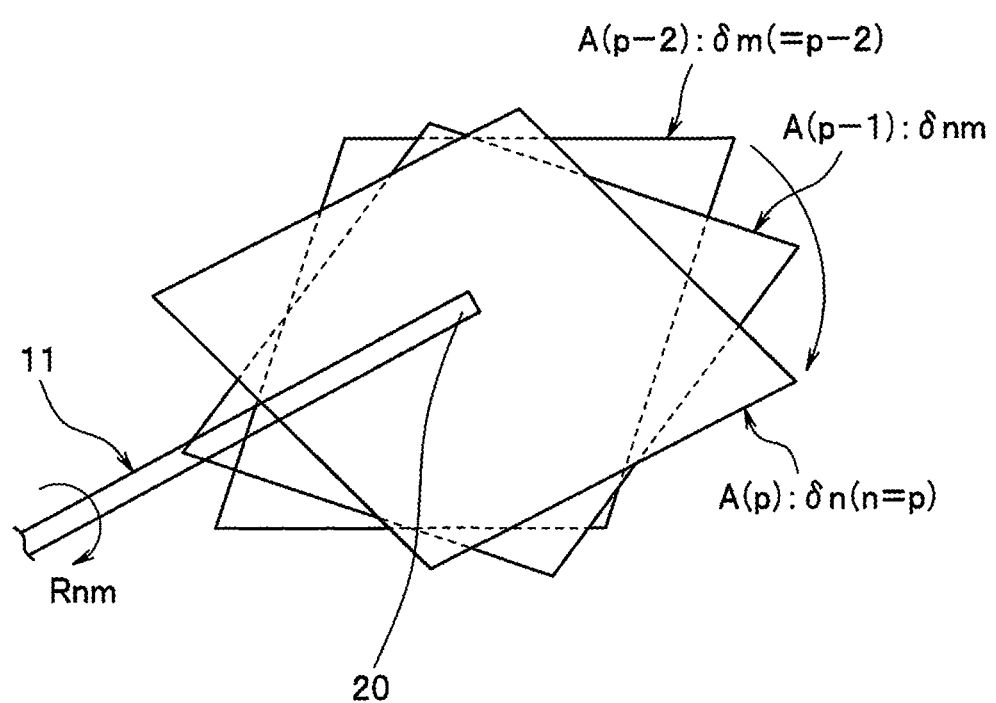
FIG. 17 is an explanatory diagram for judgment by an angular speed in FIG. 14.

Further, FIG. 17 shows a state in which a judgment is made for the angular speed Rnm in a case of a rotation angle $\delta_{p-1}$ between axial-direction rotation angles $\delta_{p-2}$ and $\delta_p$ of the distal end portion 20 when images of the target areas A(p-2), A(p-1), A(p) in FIG. 16B are picked up. In this case also, a camera-shaken image is obtained if the angular speed Rnm is equal to or larger than the threshold Thre3, and such an image is judged to be an image not to be used for pasting.

Figure 18:
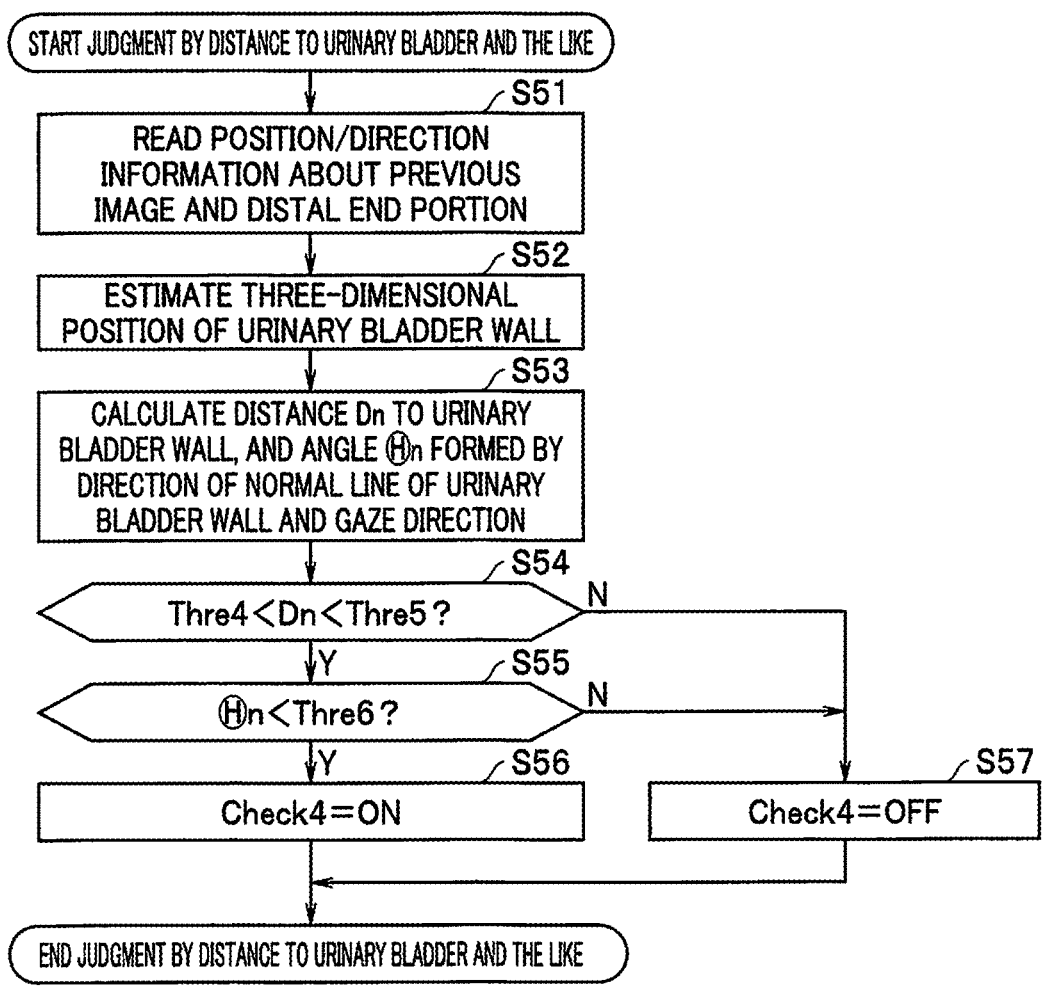
FIG. 18 is a flowchart showing details of a judgment process by a distance to a urinary bladder wall and a gaze direction in FIG. 10.

FIG. 18 shows details of the judgment process by a distance to the urinary bladder wall and a gaze direction at step S27 in FIG. 10. In FIG. 18, the judgment by the distance to the urinary bladder wall and the gaze direction is abbreviated as judgment by the distance to the urinary bladder wall and the like.

When the judgment starts, the position/direction information judging section 46b (of the pasted image judging section 31f) reads position/direction information about an endoscopic image before an endoscopic image currently acquired (abbreviated as a previous image), at first step S51.

Figure 19A:
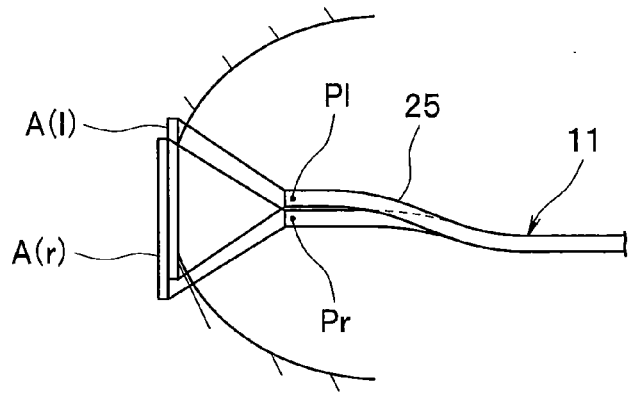
FIGS. 19A to 19C are explanatory diagrams of processes at steps S52 and S53 in FIG. 18.

At next step S52, the information-such-as-distance judging section 46c of the pasted image judging section 31f estimates a three-dimensional position of the urinary bladder wall. For example, as shown in FIG. 19A, it is possible to, by inserting the distal end side of the insertion portion 11 into the urinary bladder B and slightly changing a bending direction of the bending portion 25, for example, relative to right and left directions, set the distal end portion 20 at positions Pl, Pr which are separated in the right and left directions, and pick up images of target areas A(1), and A(r) which includes a same area. In this case, the above can be regarded as stereo image pickup means in which the image pickup section 23 is arranged at each of the two positions Pl, Pr.

Each of the positions Pl, Pr can be calculated by the magnetic sensor 8, and the information-such-as-distance judging section 46c estimates the three-dimensional position of the urinary bladder wall from two endoscopic images Img(1), and Img(r) picked up by the image pickup section 23 at the respective positions.

At next step S53, the information-such-as-distance judging section 46c calculates a distance Dn from the distal end portion 20 to the urinary bladder wall, and an angle θn formed by a direction of a normal line of the urinary bladder wall and the gaze direction of the image pickup section 23.

The distance Dn can be calculated from the three-dimensional position of the distal end portion 20 and the three-dimensional position of the urinary bladder wall. Further, the angle θn formed by the direction of the normal line of the urinary bladder wall and the gaze direction of the image pickup section 23 is calculated as shown in FIG. 19B.

Figure 19B:
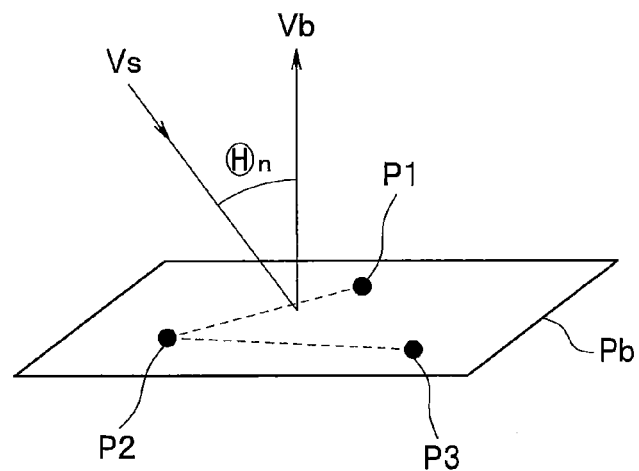
Figure 19C:
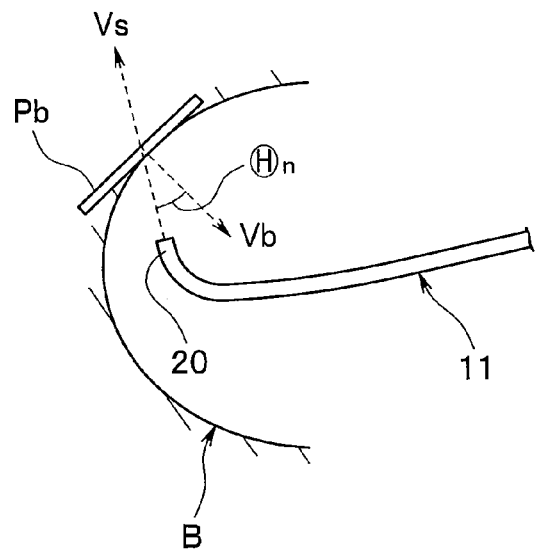

As shown in FIG. 19B, by measuring positions of three points P1, P2, and P3 relative to the urinary bladder wall surface (utilizing stereo measurement as in FIG. 19A), a urinary bladder wall surface Pb which includes the three points can be decided, and, furthermore, a normal line vector Vb vertical to the urinary bladder wall surface Pb can be calculated. Further, the angle θn formed by the normal line vector Vb and a gaze direction Vs of the image pickup section 23 can be calculated. Note that FIG. 19C shows a state of observing the urinary bladder wall surface Pb in the urinary bladder.

When the process of step S53 in FIG. 18 ends, the information-such-as-distance judging section 46c makes a judgment about whether or not the distance Dn is within a range between a lower-limit-side threshold Thre4 and an upper-limit-side threshold Thre5 set in advance, at next step SM.

Figure 20A:
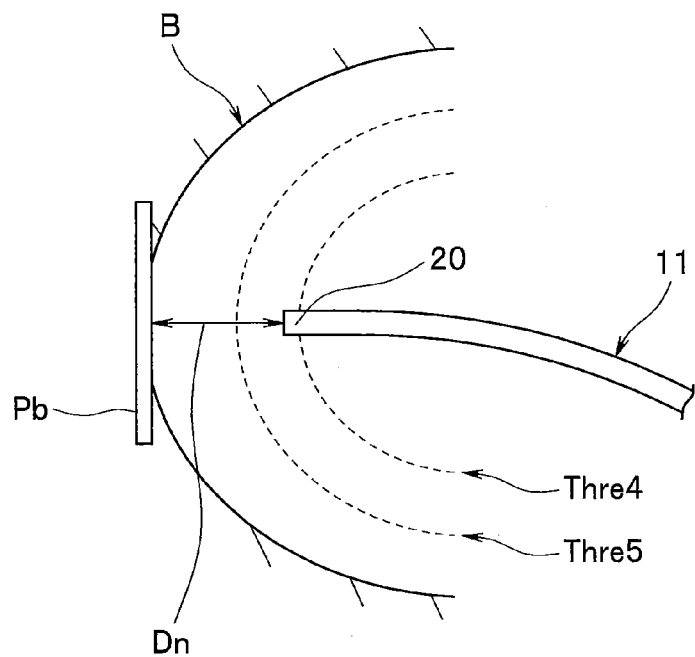
FIGS. 20A and 20B are explanatory diagrams of a process at step S54 in FIG. 18.
Figure 20B:
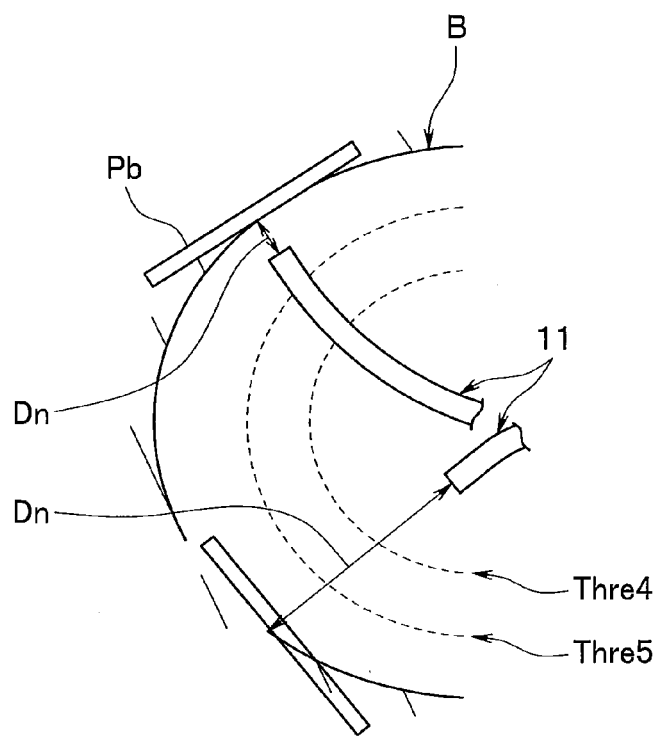

FIG. 20A shows an example of the case where an image conforms to the condition of being judged to be a pasted image. The example shown in FIG. 20A shows a case where the distance Dn from the distal end portion 20 to the urinary bladder wall surface Pb is within the range between the lower-limit-side threshold Thre4 and the upper-side-limit threshold Thre5. In comparison, an example shown in FIG. 20B shows a case where the distance Dn is smaller than the lower-limit-side threshold Thre4 and a case where the distance Dn is larger than the upper-limit-side threshold Thre5. An image is not judged as a pasted image.

When the distal end portion 20 is too near to the urinary bladder wall surface Pb or farther from the urinary bladder wall surface Pb than a certain level, an endoscopic image obtained by image pickup by the image pickup section 23 is not focused or brightness of which is not appropriate.

Therefore, as a range within which an image with appropriate focus and brightness can be picked up, a range within which the Dn is larger than the threshold Thre4 and smaller than the predetermined threshold Thre5 is set in advance as an appropriate distance to an object.

If a judgment result shows that the distance Dn is within the range between the threshold Thre4 and the threshold Thre5 at step S54 in FIG. 18, the information-such-as-distance judging section 46c makes a judgment about whether the angle θn formed by the normal line vector Vb and the gaze direction Vs is smaller than a threshold Thre6 set in advance, at next step S55.

If a judgment result shows that the angle θn is smaller than the threshold Thre6, the information-such-as-distance judging section 46c causes Check4 to be ON according to the judgment result by the information-such-as-distance judging section 46c that the picked-up endoscopic image is an image conforming to the pasting condition, at step S56.

On the other hand, if a judgment result shows that the respective conditions are not satisfied at steps S54 and S55, the information-such-as-distance judging section 46c causes Check4 to be OFF at step S57 and ends the process of FIG. 18.

Details of the pasting image process at step S12 in FIG. 9 has been described with use of FIG. 10, and FIGS. 11 to 20 showing details of the processes of S21, S23 and S25 in FIG. 10. When the pasted image judgment process ends in this way, the image pasting processing section 31d pastes the endoscopic image (picked-up image) judged as a pasted image at a corresponding position in a developed image BE as described at step S14 of FIG. 9.

In the present embodiment, in order to make it easy to recognize which position or which range (or area) on a developed image BE displayed in the second area 42 an endoscopic image displayed in the first area 41 on the monitor 7 is being picked up for, the image pickup range presenting section (or image pickup range presenting circuit) 45a of the image pasting/presentation processing section 31e makes a mark indicating an image pickup range (or image pickup area) on the developed image BE. FIGS. 21A, 21B, 21C and 21D show examples of the image pickup range by the image pickup range presenting section 45a.

Figure 21A:
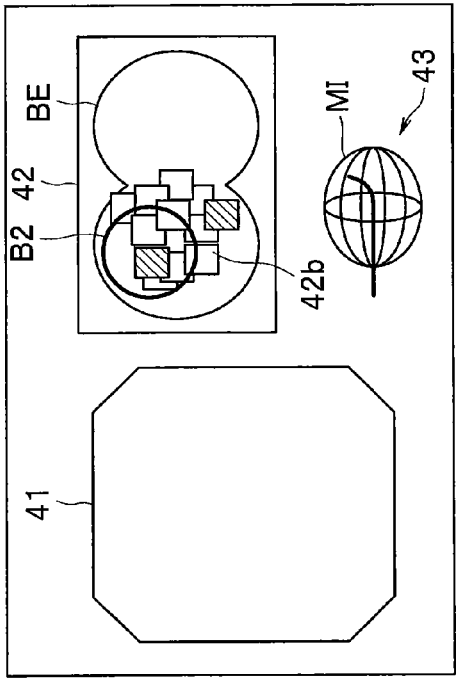
FIGS. 21A to 21D are diagrams each showing an example of presenting an image pickup range corresponding to an endoscopic image displayed in a first area, in an image displayed being pasted on a developed image.

When a frame of a range A1 is set for an endoscopic image in the first area as shown in FIG. 21A, the surgeon can easily grasp which range on a developed image BE the endoscopic image in the first area is being picked up for by displaying a frame of a corresponding image pickup range B1 on the developed image BE displayed in the second area 42, which corresponds to the range A1.

Figure 21B:
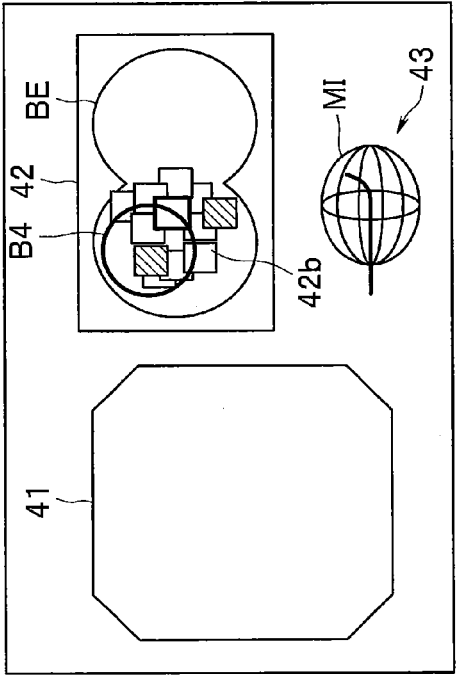
Figure 21C:
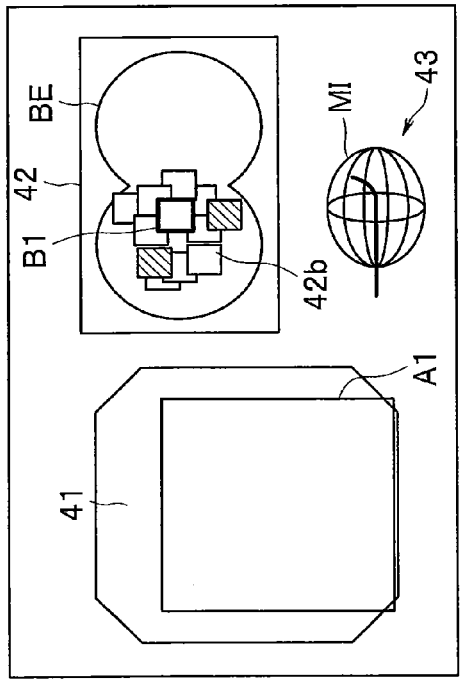

Further, as shown in FIG. 21B or FIG. 21C, an image pickup range on a developed image BE corresponding to a range for which an endoscopic image in the first area is being picked up, by a circular frame B2 or a rectangular frame B3. By doing so, an effect substantially similar to the case of FIG. 21A is obtained.

Figure 21D:
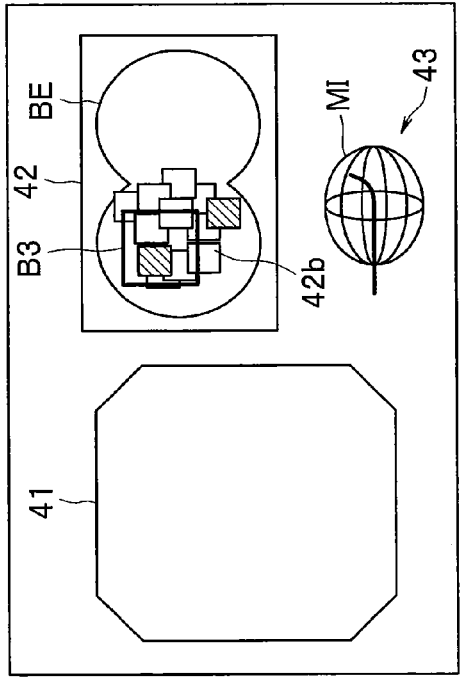
Figure 22A:
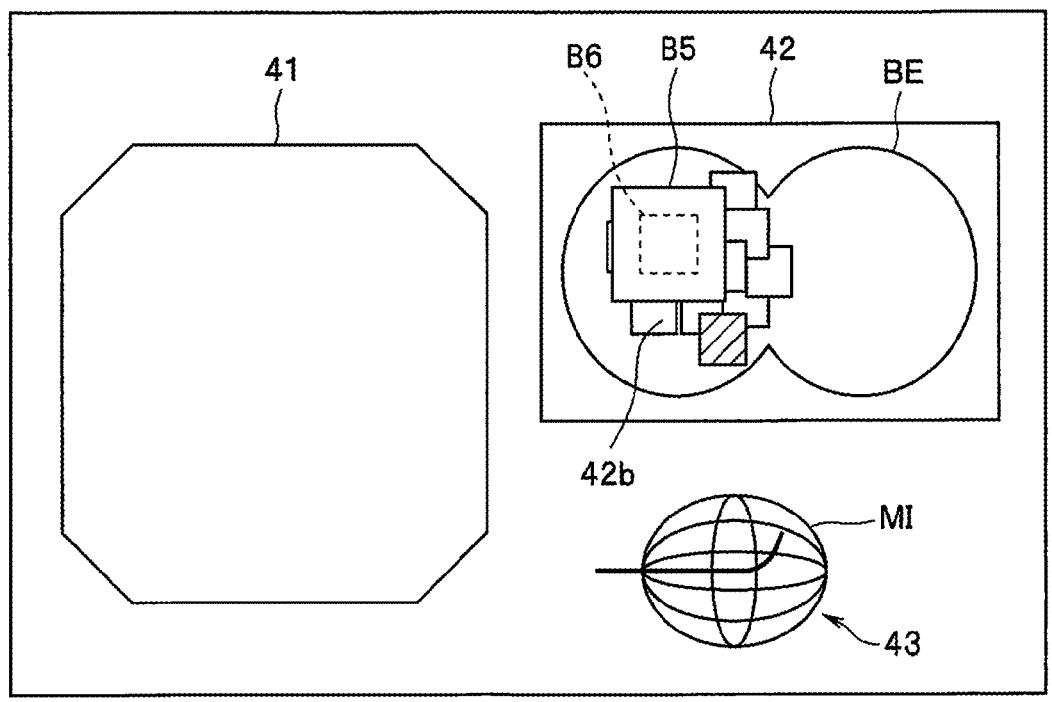
FIG. 22A is an explanatory diagram of a presentation example in which, at time of pasting a next pasted image after pasting a newest pasted image, the newest pasted image is reduced and presented.

Further, as shown in FIG. 21D, an image pickup range on a developed image BE corresponding to a range for which an endoscopic image in the first area 41 is being picked up is displayed by a colored area B4 which is colored, for example, with blue. By doing so, an effect substantially similar to the case of FIG. 21A is obtained. Further, image pasting may be performed as shown in FIG. 22A.

At the time of pasting a next endoscopic image after pasting an endoscopic image (picked-up image) picked up in the latest state at a corresponding position on a developed image BE as a pasted image B5 with a size substantially corresponding to an image-picked-up area (an image pickup range) as described above, the endoscopic image may be reduced as a pasted image B6 indicated by a dotted line. Note that, when the endoscopic image is caused to be the pasted image B6, a part of the pasted image hidden by the pasted image B5, outside the pasted image B6 is displayed.

Figure 22B:
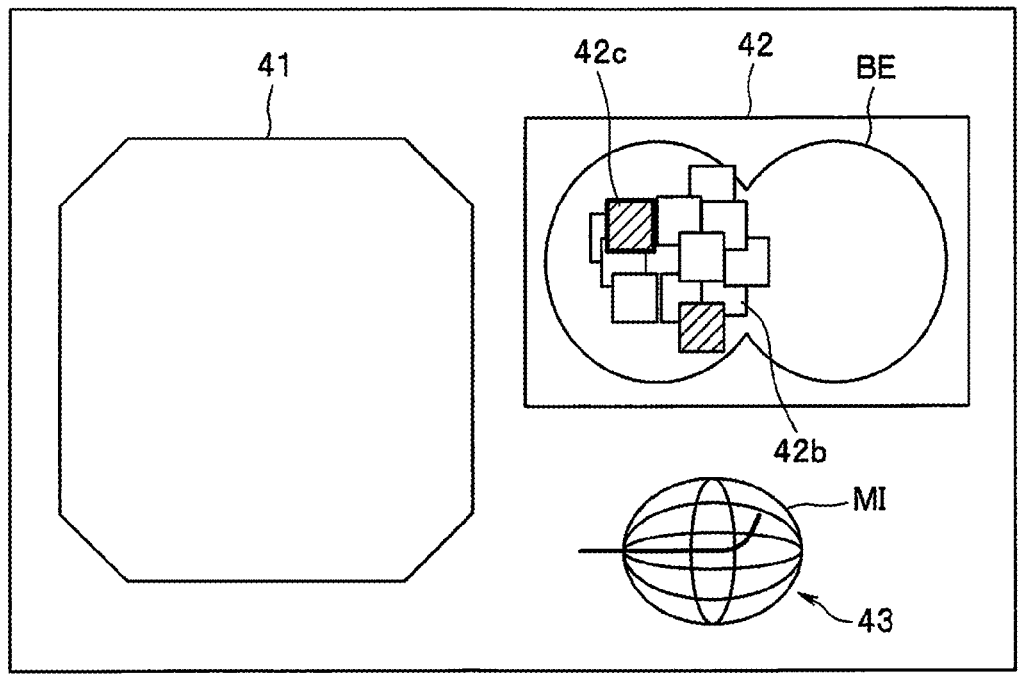
FIG. 22B is a diagram showing an example of setting a position on a developed image corresponding to an endoscopic image displayed in the first area at a center of the developed image to present the image.
Figure 22B:
Figure 22B:
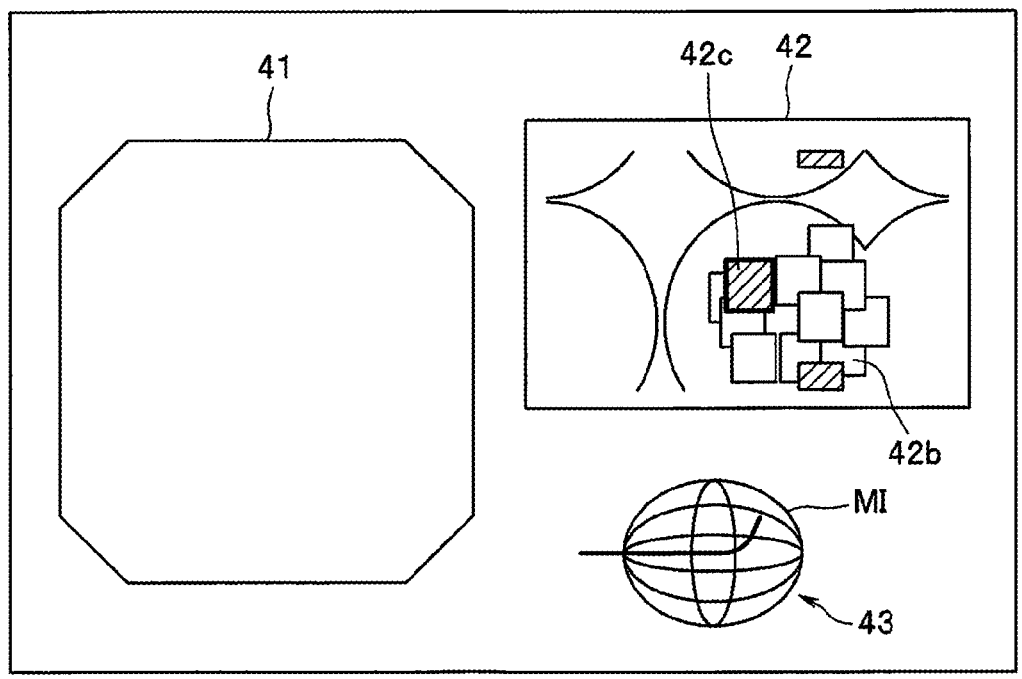

Further, a display position (presentation position) on the developed image BE may be adjusted and displayed by the presentation position adjusting section (or presentation position adjusting circuit) 45b instead of using the image pickup range presenting section 45a. FIG. 22B shows a presentation (display) example in this case.

As shown in FIG. 22B, a developed image BE is moved and display so that an image 42c pasted on the developed image BE correspondingly to an endoscopic image displayed in the first area is located at the center of the developed image BE. That is, the developed image BE and the like displayed on the monitor 7 before being adjusted by the presentation position adjusting section 45b is shown on a left side of FIG. 22B, and, on the developed image BE, an image 42c corresponding to the endoscopic image displayed in the first area 41 is difficult to recognize because of existence of other images 42b and the like.

Therefore, the presentation position adjusting section 45b adjusts and displays the developed image BE so that the image 42c is located at a center of the second area 42 as shown on a lower side of FIG. 22B, in order to cause (an image pickup range of) the image 42c corresponding to the endoscopic image to be easily recognized.

Further, in the present embodiment, it is possible to select the presentation angle adjusting section (or presentation angle adjusting circuit) 45c by selection from the presentation selecting section 38a by the surgeon.

In the present embodiment, the presentation angle adjusting section 45c of the image pasting/presentation processing section 31e adjusts an angle (generally) indicating the orientation of an image to be pasted on a developed image BE in the second area 42 corresponding to an endoscopic image in the first area 41 so that the surgeon can easily grasp each portion of both images, as described below. Further, the presentation angle adjusting section 45c has a function of image adjusting means or an image adjusting section which performs display (presentation) so that each orientation of an endoscopic image (picked-up image) picked up by the image pickup means is caused to correspond to each orientation of a pasted image on a developed image BE, as described below.

Further, the presentation angle adjusting section 45c can be said to have a function of adjusting the orientation or angle of a developed image BE so that, relative to upward, downward, right and left directions in a case where a picked-up image is displayed in a first display area by the first area 41, upward, downward, right and left directions of an image to be pasted onto the developed image BE as a planar model image displayed in a second display area by the second area 42 correspond, respectively, on the monitor 7 as an image display apparatus.

In the case of inserting the distal end side of the insertion portion 11 into the urinary bladder to observe the inner surface of the urinary bladder, for example, a rear wall side of the urinary bladder can be observed without bending the bending portion 25 much. In such a case, when an image is picked up by the image pickup section 23 and displayed as an endoscopic image in the first area 41, the endoscopic image is displayed in a manner that upward, downward, right and left orientations of the endoscopic image correspond to normal upward, downward, right and left orientations, respectively, in advance. The upward, downward, right and left orientations in this case correspond to upward, downward, right and left directions, respectively, in a state that the bending portion 25 is not bent.

However, in a case of observing an entrance-side inner surface of the urinary bladder B where the insertion portion 11 is inserted, it is necessary to bend the bending portion 25 as much as the bending portion 25 is caused to be reversed by more than 90°. When the bending portion 25 is caused to bend so much, the upward, downward, right and left orientations in the case of the image pickup section 23 provided at the distal end portion 20 performing image pickup change depending on a bending direction of the bending portion 25. An endoscopic image displayed in the first area 41 changes according to an attitude due to bending and the like on the distal end portion 20 side caused at the time of the image pickup section 23 performing image pickup.

If an orientation of an endoscopic image displayed in the first area 41 and an orientation of an image pasted on a developed image BE do not correspond to each other, a case may occur where it is difficult to recognize whether the images are same images or not (in a case where a plurality of images are pasted), and, in such a case, it becomes difficult to grasp which site or area in the urinary bladder B an image is being picked up for.

Therefore, in the present embodiment, an orientation of an image pasted on a developed image BE, in other words, an angle of the developed image BE, which is an image onto which an endoscopic image is to be pasted, is adjusted so that it is possible to easily recognize or grasp whether both images are same images or not, as described below.

Figure 23A:
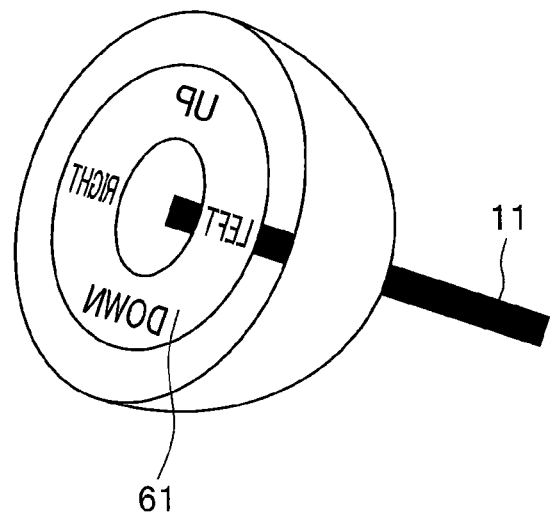
FIG. 23A is an explanatory diagram showing a state of inserting the insertion portion into a three-dimensional model of the urinary bladder and picking up an image of an observation target from a front side.

FIGS. 23A to 27 show an explanatory diagram of the operation. FIG. 23A shows an observation target 61 with characters attached at typical four positions on an inner surface of a three-dimensional model of the urinary bladder B, and FIG. 23B shows an endoscopic image (displayed in the first area 41) which is obtained by picking up an image of the observation target 61 from a front.

Figure 24A:
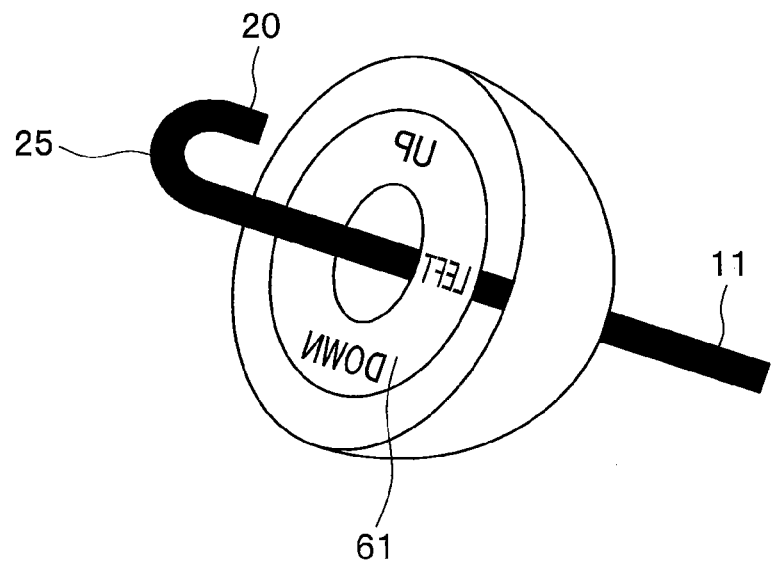
FIG. 24A is an explanatory diagram showing a state of inserting the insertion portion into the three-dimensional model of the urinary bladder, causing the insertion portion to bend so much as the insertion portion is reversed in an upward direction, and picking up an image of an observation target from a rear side.
Figure 24B:
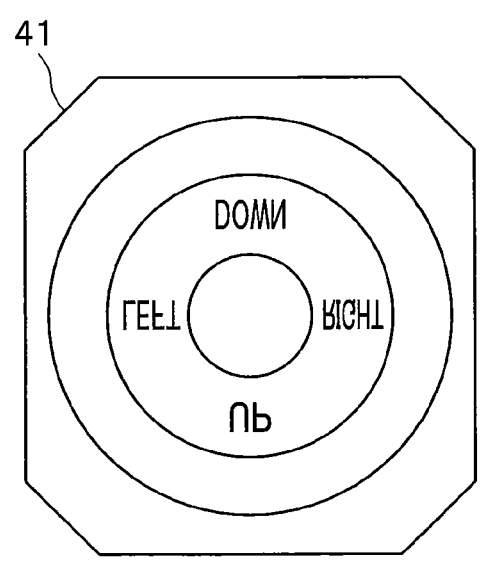
FIG. 24B is an endoscopic image when image pickup has been performed in FIG. 24A.

FIG. 24A shows a state of causing the distal end side of the insertion portion 11 to bend much in the upward direction to observe the observation target 61 shown in FIG. 23A from a back side. An endoscopic image in that case is as shown in FIG. 24B.

Figure 25A:
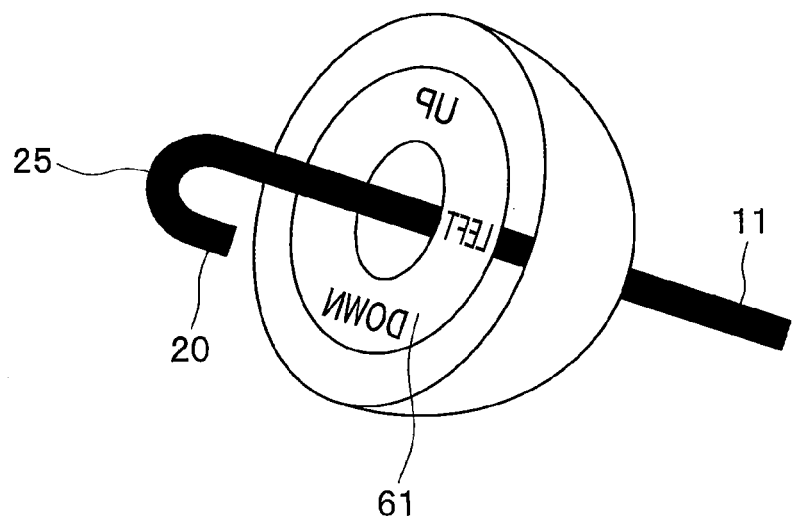
FIG. 25A is an explanatory diagram showing a state of inserting the insertion portion into the three-dimensional model of the urinary bladder, causing the insertion portion to bend so much as the insertion portion is reversed in a downward direction, and picking up an image of an observation target from a rear side.
Figure 25B:
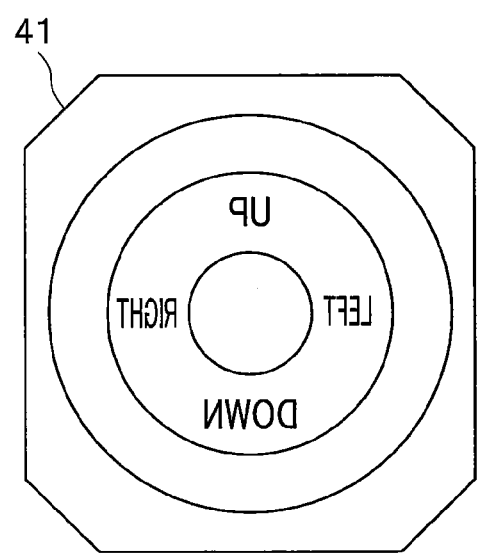
FIG. 25B is an endoscopic image when image pickup has been performed in FIG. 25A.

FIG. 25A shows a state of causing the distal end side of the insertion portion 11 to bend much in the upward direction to observe the observation target 61 shown in FIG. 23A from the back side. An endoscopic image in that case is as shown in FIG. 25B.

A relationship among the respective upward, downward, right and left directions of the first area 41 differs according to each bending state of the insertion portion 11. When images are pasted onto the second area 42 in that state, orientation relationships among the respective images pasted onto the second area 42 are not uniformed, and, therefore, a state occurs in which the images are not related to one another. In the present embodiment, an angle of a developed image BE excluding an image 42d pasted onto the developed image BE is adjusted to perform display as in FIGS. 26 and 27.

Figure 23B:
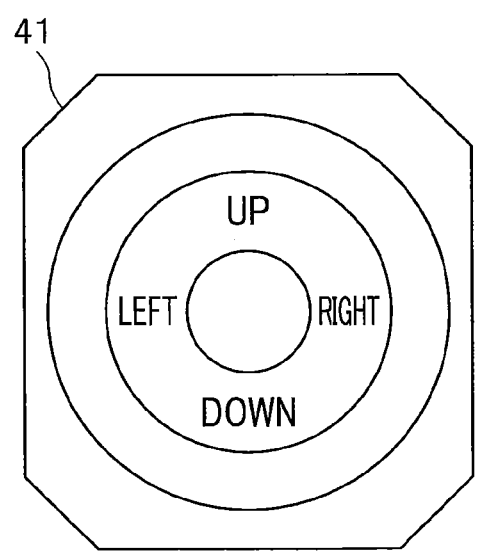
FIG. 23B is an endoscopic image when image pickup has been performed in FIG. 23A.
Figure 26:
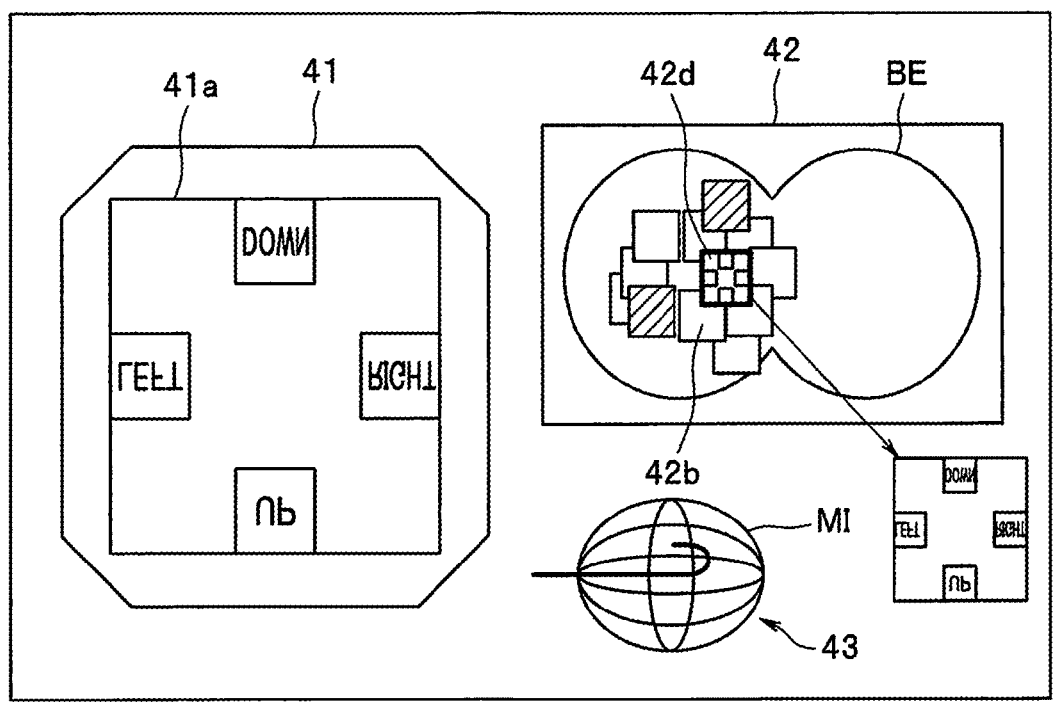
FIG. 26 is an explanatory diagram showing an example of displaying an image pasted on a developed image, causing an orientation of the image to correspond to an orientation of display of the endoscopic image in FIG. 24B.
Figure 27:
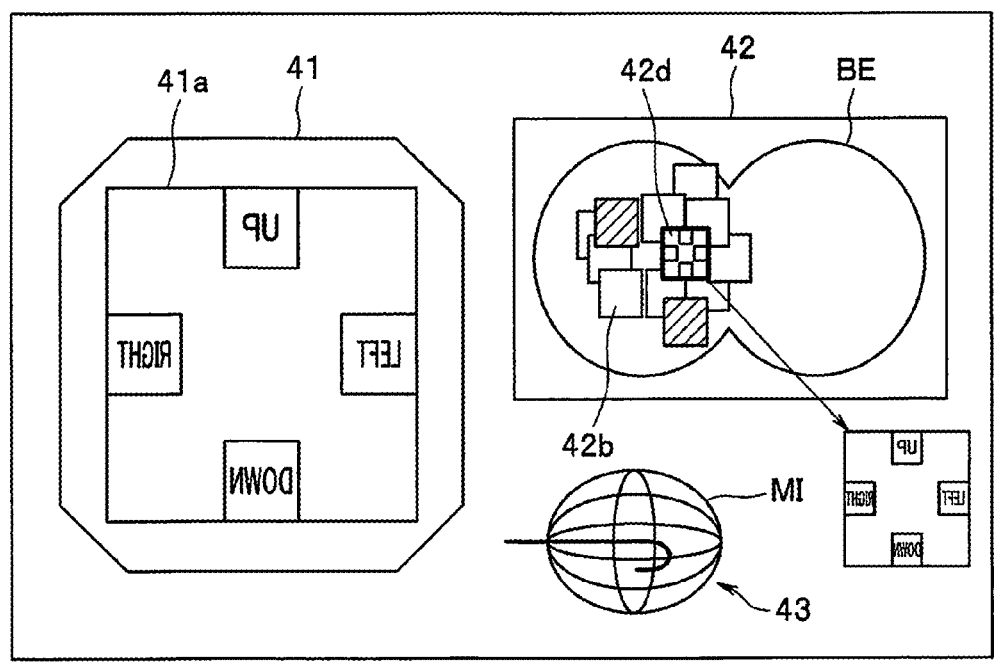
FIG. 27 is an explanatory diagram showing an example of displaying an image pasted on a developed image, causing an orientation of the image to correspond to an orientation of display of the endoscopic image in FIG. 25B.

Since respective orientations of an endoscopic image 41a displayed in the first area 41 correspond to respective orientations of an image 42d pasted on a developed image BE displayed in the second area 42, respectively, as shown in FIGS. 26 and 27, the surgeon can easily grasp that both images are same images; and, since the orientation relationships among pasted images are uniformed, the images are correctly related. Though the case of FIG. 23A or FIG. 23B is not shown, the case is similar to the cases of FIGS. 26 and 27. Note that, though, in the case of causing orientations of an endoscopic image displayed in the first area 41 to correspond to orientations of an image pasted and displayed on a developed image BE displayed in the second area 42, the orientations (angle) of the BE are changed at a position of the image 42d pasted on the developed image BE is changed in FIGS. 26 and 27, it is also conceivable to perform adjustment (to form the image adjusting means) so that the orientations of both images correspond by causing the developed image BE to rotate around its central position. Note that, though description has been made on the case where the bending portion 25 is caused to bend in a particular direction to perform image pickup in FIGS. 24A to 27, the present embodiment can be applied to a case of performing image pickup in a direction different from that of the shown case.

Figure 28:
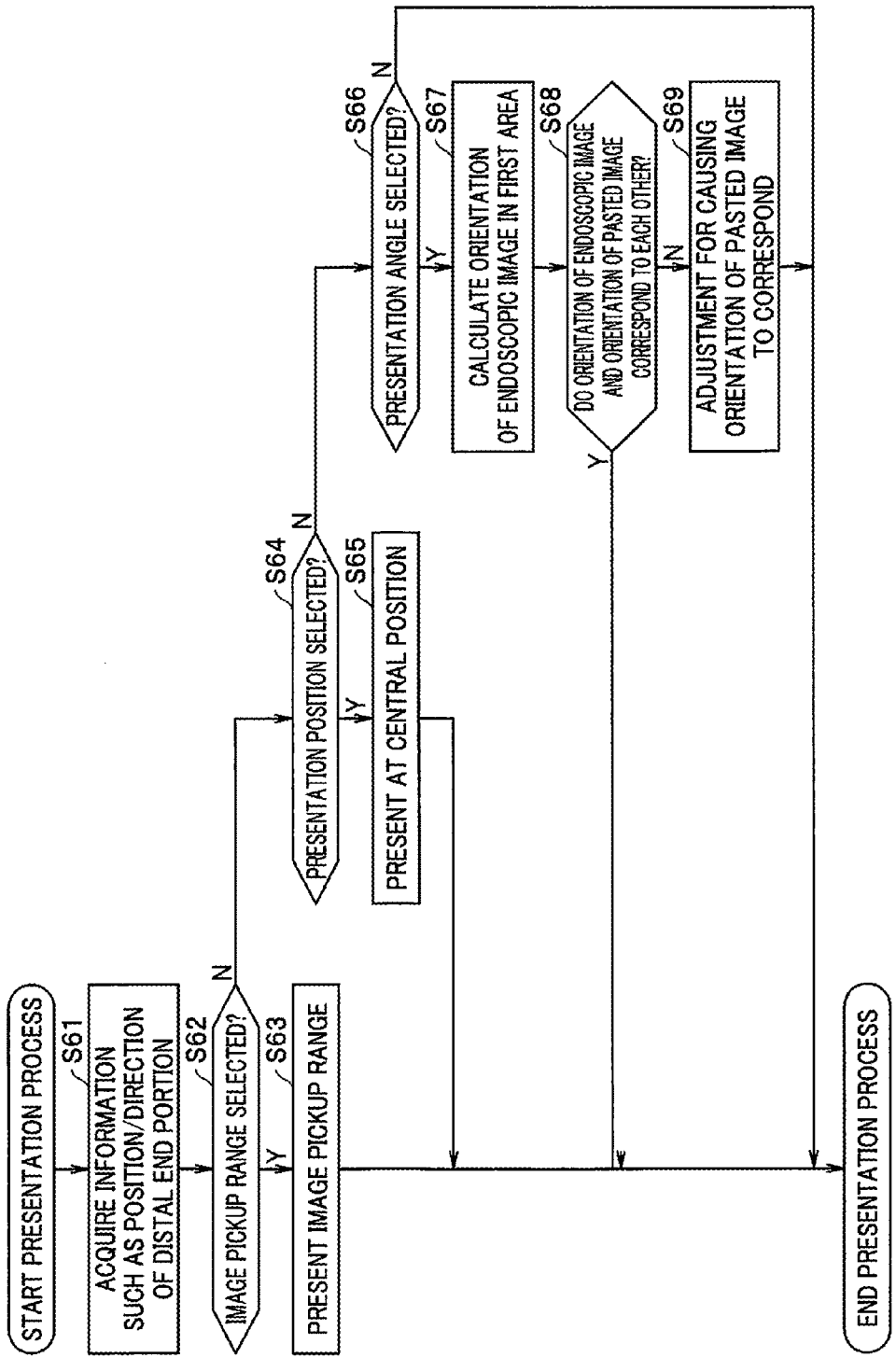
FIG. 28 is a flowchart showing an example of a process at step S15 in FIG. 9.

FIG. 28 shows details of the processes of steps S15 to 16 in FIG. 9. An image pasted onto the developed image BE is judged to be a pasted image 42a, and the pasted image 42a is pasted at a corresponding position in the developed image BE at step S14. When the pasting is decided, a presentation process for deciding a presentation (display) method starts as shown in FIG. 28.

At first step S61, the presentation angle adjusting section 45c of the image pasting/presentation processing section 31e acquires information about an attitude of the image pickup section 23 on the distal end side of the insertion portion 11 perform image pickup (a state of FIGS. 23A, 24A, 25A or the like) based on position/direction information and insertion shape information by the position/direction detecting section 34, and calculates a pasting position on the developed image BE. At next step S62, the image pasting/presentation processing section 31e makes a judgment about whether or not presentation of an image pickup range of an endoscopic image has been selected from the presentation selecting section 38a by the surgeon.

If the selection has been made, the image pasting/presentation processing section 31e presents an image pickup range of a current endoscopic image on the developed image BE like the presentation examples of FIGS. 21A to 21D at next step S63, and ends the process of FIG. 28.

If the selection of an image pickup range is not performed at step S62, the image pasting/presentation processing section 31e makes a judgment about whether or not a presentation position has been selected by the presentation selecting section 38a, at step S64.

If the selection has been made, the image pasting/presentation processing section 31e presents the image pickup range of the current endoscopic image in a manner that the image pickup range is located at a central position on the developed image BE like the presentation examples of FIG. 22A at next step S65, and ends the process of FIG. 28.

If the selection of a presentation position is not performed at step S64, the image pasting/presentation processing section 31e makes a judgment about whether or not a presentation angle has been selected from the presentation selecting section 38a, at step S66. If the selection has been made, the image pasting/presentation processing section 31e calculates orientations of an endoscopic image to be displayed in the first area 41, at next step S67. Note that the orientations of the endoscopic image to be displayed in the first area 41 are set so as to be determined according to an attitude of the image pickup section 23 to be a reference.

At next step S68, the presentation angle adjusting section 45c makes a judgment about whether or not the orientations of the endoscopic image displayed in the first area 41 correspond to orientations of the pasted image 42a pasted at a corresponding position on the developed image BE.

If a judgment result shows that the directions do not correspond, the presentation angle adjusting section 45c performs angle adjustment of the developed image BE so that the orientation of the pasted image 42a pasted on the developed image BE corresponds to the orientation of the endoscopic image displayed in the first area 41 at next step S69 (see the presentation examples in FIGS. 26 and 27), and ends the process of FIG. 28.

On the other hand, if a judgment result shows that the directions correspond in the judgment process at step S66, the process in FIG. 28 also ends.

In this way, the developed image BE on which the pasted image 42a is pasted is displayed on the monitor 7 together with the endoscopic image and the like. If the process of FIG. 28 is performed, it is possible to easily grasp an image pickup range of an endoscopic image which is currently being picked up (observed) as shown in FIGS. 21A to 21D. Further, as shown in FIG. 22A, it is possible to easily grasp the image pickup range of the current endoscopic image. Further, as shown in FIGS. 26 and 27, since the orientation of the endoscopic image corresponds to the orientation of the pasted image 42a pasted on the developed image BE, the surgeon can easily grasp that both images are a same image.

In the above description, the case where the insertion portion 11 with the bending portion 25 capable of freely bending provided on the distal end side of the insertion portion 11 is the flexible endoscope 3 has been described.

In comparison, there may be a case where a rigid endoscope as an endoscope having a rigid insertion portion is used to observe an inside of a urinary bladder. Therefore, in the endoscope system 1 shown in FIG. 1 or 2, it is also possible for the surgeon to select and use any desired endoscope among the endoscope 3 and rigid endoscopes 3B, 3C, and 3D shown in FIG. 29.

Figure 29:
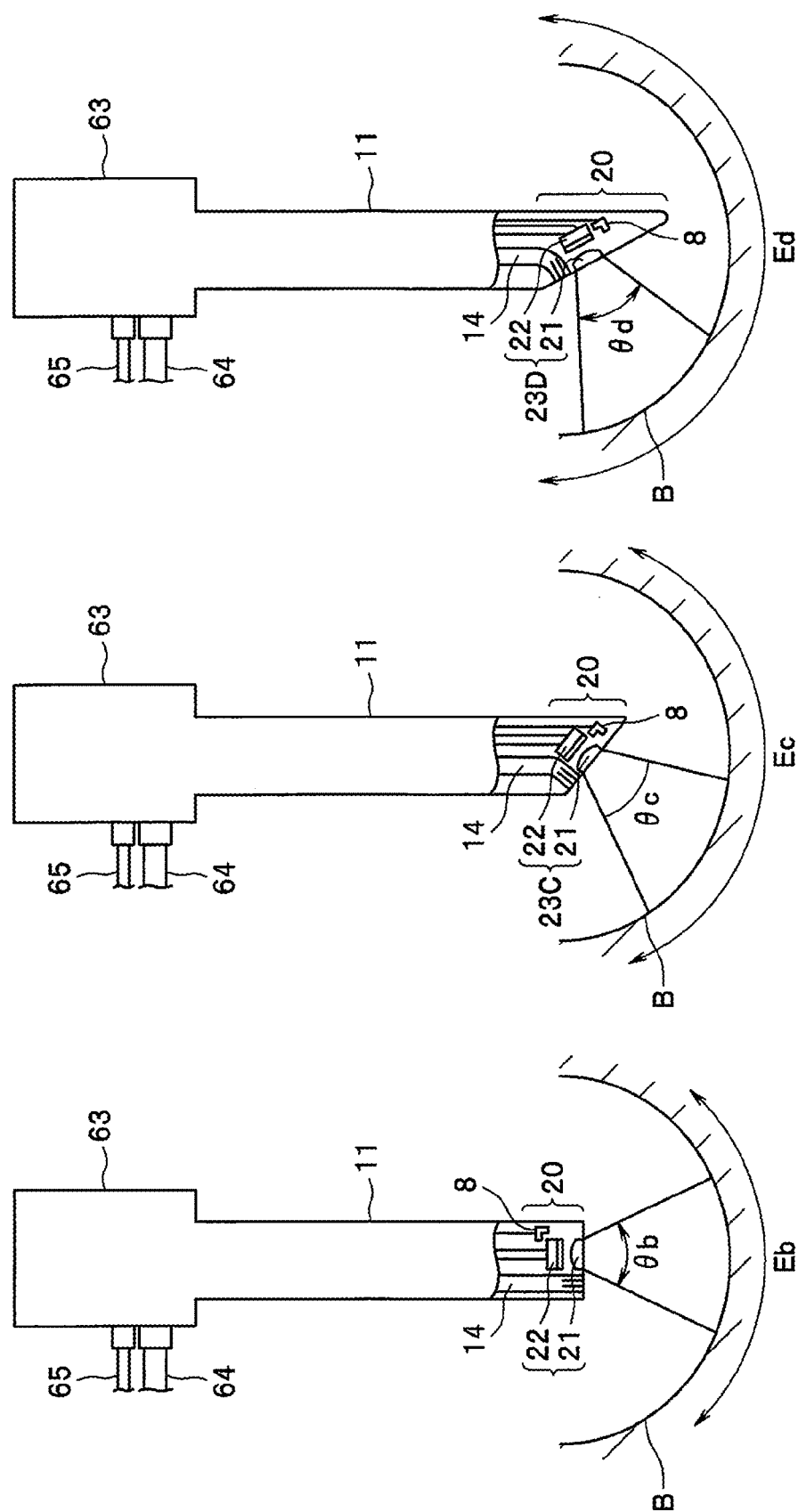
FIG. 29 is a diagram showing a configuration of a rigid endoscope.

FIG. 29 shows, for example, three kinds of rigid endoscopes 3B, 3C, and 3D having different view angles and the like. Each endoscope 3I (I=B, C, D) has a rigid insertion portion 11, a grasping portion 63 at a rear end (proximal end) of the endoscope 3I, a light guide cable 64 detachably extended in a vicinity of the grasping portion 63, and a signal cable 65. An end portion of the light guide cable 64 not shown is detachably connected to the light source apparatus 4 shown in FIG. 2. Illuminating light supplied from the light source apparatus 4 is transmitted by the light guide cable 64 and the light guide 14 in the endoscope 3I and emitted from a distal end surface of the light guide 14 arranged at the distal end portion 20 of the insertion portion 11 (via an illumination lens not shown).

The distal end portion 20 is provided with an image pickup section 23I configured with the objective lens 21 and the CCD 22, and it is possible to pick up an image of an inner surface of the urinary bladder by the image pickup section 23I. Further, the magnetic sensor 8 constituting the image pickup information acquiring means is arranged near or in a vicinity of the image pickup section 23I. Note that, though the example shown in FIG. 29 adopts a configuration in which the CCD 22 constituting the image pickup means is arranged at an image forming position of the objective lens 21, it is also conceivable to adopt a configuration in which a connecting member, such as a TV camera, provided with the CCD 22 is connected to a rear end of an optical endoscope having the rigid insertion portion 11, and the magnetic sensor 8 constituting the image pickup information acquiring means is arranged in a vicinity of the CCD 22 of the connecting member. Furthermore, it is also conceivable to provide a member connected to the image pickup means in a state that a form does not change with time, with the magnetic sensor 8 or the like constituting the image pickup information acquiring means capable of detecting position information and gaze information about the image pickup means. That is, the image pickup information acquiring means for detecting the position information and gaze information about the image pickup means may be provided in a vicinity of the image pickup means or on the member connected to the image pickup means.

Note that, since a position and an image pickup range where an image of an inside of a predetermined organ is actually picked up by the image pickup means or the CCD 22 forming the image pickup section are decided substantially by the objective lens 21 forming an objective optical system arranged at the distal end of the insertion portion, the position information and gaze information about the image pickup section may be replaced with position information and gaze information (optical axis direction information) about the objective lens 21. In other words, the image pickup information acquiring section which is provided in the member connected in the vicinity of or to the image pickup section and detects (or acquires) the position information and gaze information about the image pickup section may be replaced with the image pickup information acquiring section which constitutes the image pickup section and which (forms an optical image of a predetermined organ and) detects (or acquires) the position information and gaze information about the objective optical system used for image pickup.

A range within which image pickup in the urinary bladder by the image pickup section 23I is possible differs according to a view angle $\theta i$ (i=b, c, d) as shown in FIG. 29.

In an image pickup section 23B, a view angle $\theta b$ along a forward viewing direction with a longitudinal direction of the insertion portion 11 as a center is obtained. In an image pickup section 23C, an oblique-direction view angle $\theta c$ with a direction forming a predetermined angle relative to the longitudinal direction of the insertion portion 11 as a center is obtained. In an image pickup section 23D, an oblique-direction view angle $\theta d$ forming a larger angle relative to the longitudinal direction of the insertion portion 11 than that of the image pickup section 23C is obtained. As shown in FIG. 29, the view angles satisfy $\theta b < \theta c < \theta d$.

Thus, in the case of the rigid endoscope 3I, the range within which observation is possible is restricted by the view angle $\theta i$ of the rigid endoscope 3I when the rigid endoscope 3I is inserted in the urinary bladder.

Since the view angle θi differs as shown in FIG. 29, there may be a case where the rigid endoscope 3I is exchanged when the inside of the urinary bladder of the one patient P is examined.

In the case of exchanging the rigid endoscope 3I as above, there may be a case, if a plurality of pasted images exist on a developed image BE, it becomes difficult to recognize a pasted image corresponding to an endoscopic image which is being observed with a rigid endoscope 3I currently used.

Figure 30:
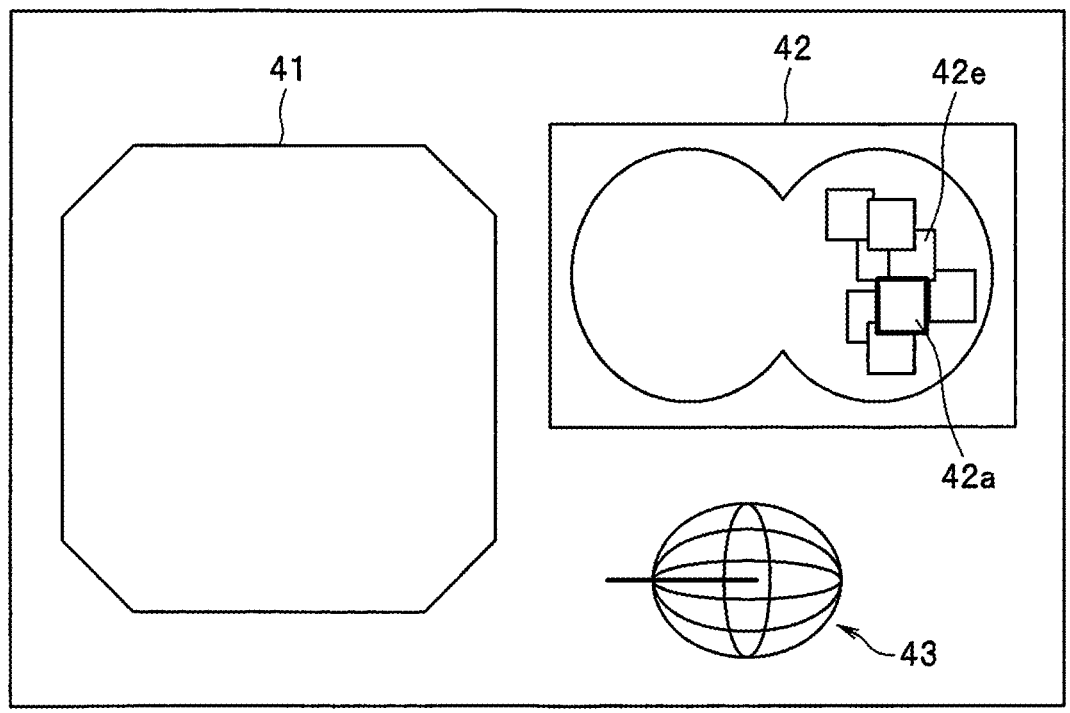
FIG. 30 is a diagram showing a display example of a developed image in a case where the rigid endoscope is used.

Therefore, as shown in FIG. 30, it is also conceivable to blur pasted images observed with rigid endoscopes which are not currently being used and clearly display a pasted image 42a observed with the rigid endoscope which is currently being used. That is, in FIG. 30, blurred images are indicated by reference numeral 42e. Note that the blurred images 42e can be displayed with a lowered luminance level, chroma, and the like. Alternatively, it is also conceivable to cause a color tone of the blurred images 42e to be monochrome so that difference from the pasted image 42a observed with the currently used rigid endoscope can be recognized.

Further, as shown in FIG. 29, the view angle differs according to a kind of rigid endoscope used, and the range within which observation is possible in the urinary bladder is restricted. Therefore, since the range in the case of observing the inside of the urinary bladder is restricted according to the kind of rigid endoscope used, as shown in FIG. 29, a developed image to be actually displayed may be changed. In FIG. 29, a rough range within which image pickup is possible according to the view angle θi of the rigid endoscope 3I is indicated by Ei.

Figure 31:
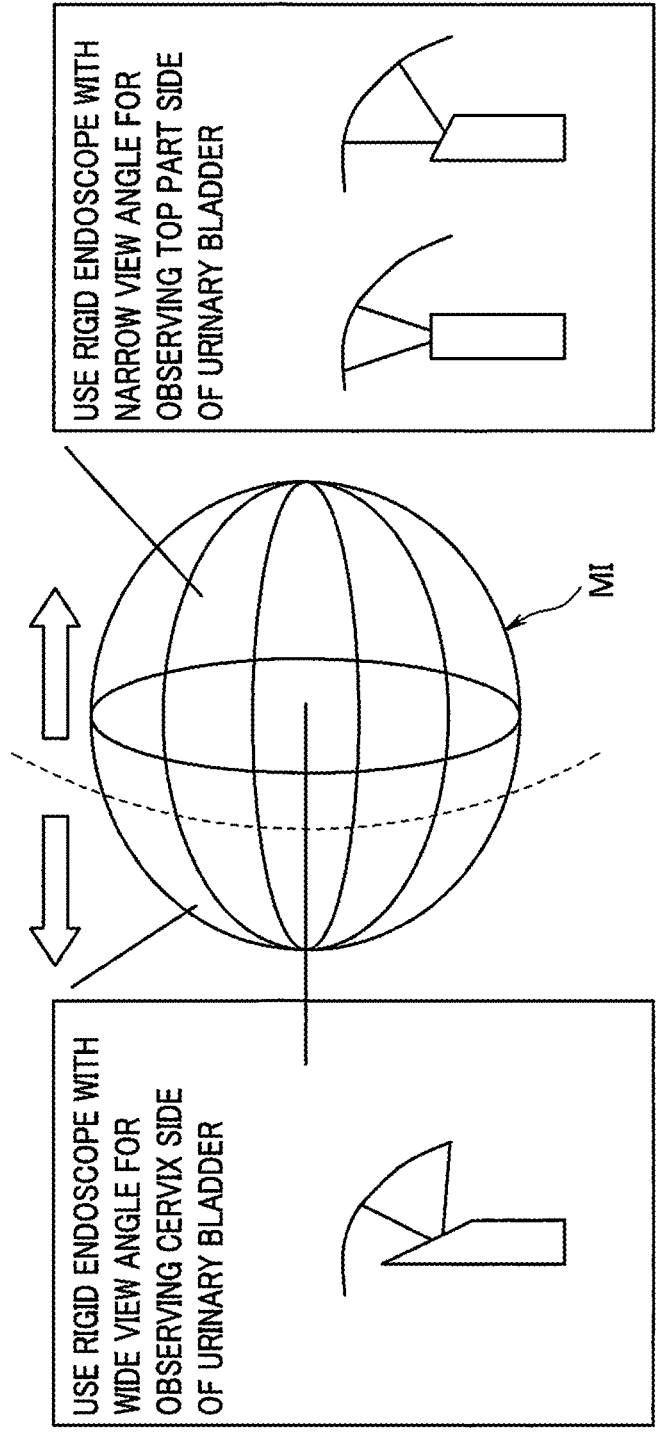
FIG. 31 is an explanatory diagram of a case of changing display of a developed image in the case where the rigid endoscope is used.

FIG. 31 shows an explanatory diagram of the case. FIG. 31 shows a 3D model image M1 used in a case of generating a developed image at a center, and a range used for generating the developed image (a dotted line indicates a boundary of the range) changes according to a width of a view angle. Thus, the display range of a developed image actually used may be adjusted according to the kind or view angle of rigid endoscope.

More specifically, in a case of the rigid endoscope 3D with a wide view angle for observing the cervix RP side of the urinary bladder B, the dotted line to be a boundary moves to a left side. In comparison, in a case of the rigid endoscopes 3B, and 3C with a narrow view angle for observing a top part side of the urinary bladder, the dotted line moves to the right side.

That is, it is conceivable to, in a case of image pickup means with a wide view angle, widen the area for developed image BE and, in a case of image pickup means with a narrow view angle, reduce the area for developed image BE. The image pasting/presentation processing section 31e constituting the image pasting/presenting means may change the presentation method by changing the area size and color tone of a developed image BE as a planar model image according to the kind of the image pickup means, or the like. Further, the image pasting/presentation processing section 31e may change the method for presentation on a developed image BE by changing a color tone or size of a pasted image pasted and presented on the developed image BE according to the kind of the image pickup means, or the like.

Note that FIGS. 32 to 38 show explanatory diagrams of conversion among coordinate systems and a case of pasting an endoscopic image onto a developed image BE in the present embodiment.

Figure 32:
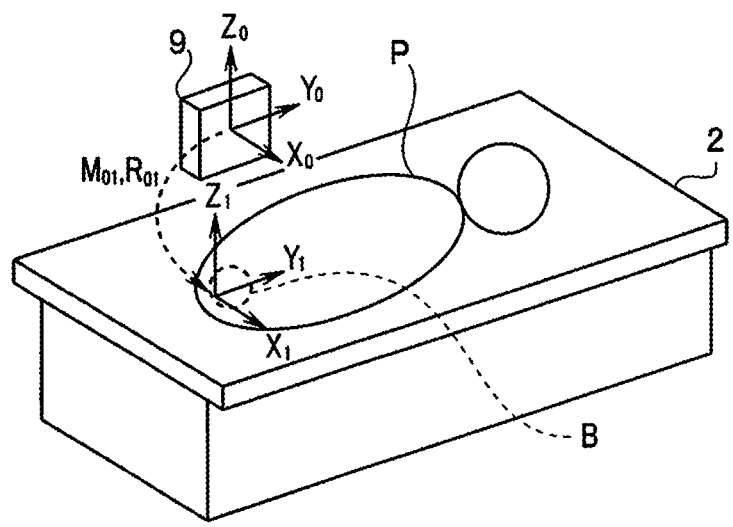
FIG. 32 is an explanatory diagram of a relationship between a coordinate system of a magnetic field generating apparatus and a coordinate system of a urinary bladder B of a patient P on a bed.

FIG. 32 is a diagram for illustrating a relationship between coordinate system of the magnetic field generating apparatus 9 and a coordinate system of the urinary bladder B of the patient P on the bed 2. The position/direction detecting section 34 generates position/direction information with the first coordinate system $(X_0Y_0Z_0)$ of the magnetic field generating apparatus 9 as a reference in real time.

Therefore, at step S6 in FIG. 9, the CPU 31 decides a position and direction of the entrance to the urinary bladder B as a reference position and a reference direction, and converts position/direction information of the position/direction detecting section 34 to position/direction information of the coordinate system $(X_1Y_1Z_1)$ with the entrance to the urinary bladder B as a reference according to next equations (4) and (5) as shown in FIG. 32.

$$P_1 = R_{01}P_0 + M_{01} \qquad (4)$$

$$V_1 = R_{01}V_0 \qquad (5)$$

Here, $P_0$ and $V_0$ are position and direction vectors, respectively, in the first coordinate system $(X_0Y_0Z_0)$ which is a coordinate system with the magnetic field generating apparatus 9 as a reference. An $R_{01}$ indicates a rotation matrix shown by a next equation (6), and $M_{01}$ indicates a translation matrix shown by a next equation (7).

[Equation 6]

$$R_{01} = \begin{pmatrix} r_{00} & r_{01} & r_{02} \\ r_{10} & r_{11} & r_{12} \\ r_{20} & r_{21} & r_{22} \end{pmatrix} \qquad (6)$$

[Equation 7]

$$M_{01} = \begin{pmatrix} m_{x01} \\ m_{y01} \\ m_{z01} \end{pmatrix} \qquad (7)$$

Therefore, a point $(x_0, y_0, z_0)$ on the first coordinate system $(X_0Y_0Z_0)$ is converted to a point $(x_1, y_1, z_1)$ on the intermediate coordinate system $(X_1Y_1Z_1)$ as shown by a next equation (8).

[Equation 8]

$$\begin{pmatrix} x_1 \\ y_1 \\ z_1 \end{pmatrix} = \begin{pmatrix} r_{00} & r_{01} & r_{02} \\ r_{10} & r_{11} & r_{12} \\ r_{20} & r_{21} & r_{22} \end{pmatrix} \begin{pmatrix} x_0 \\ y_0 \\ z_0 \end{pmatrix} + \begin{pmatrix} m_{x01} \\ m_{y01} \\ m_{z01} \end{pmatrix} \qquad (8)$$

When position and direction vectors detected by the position/direction detecting section 34 when insertion of the distal end portion 20 of the endoscope into the urinary bladder B is detected are indicated by $P'_0$ and $V'_0$, the translation matrix $M_{01}$ is determined by a following equation (9).

$$M_{01} = -P'_0 \qquad (9)$$

Figure 33:
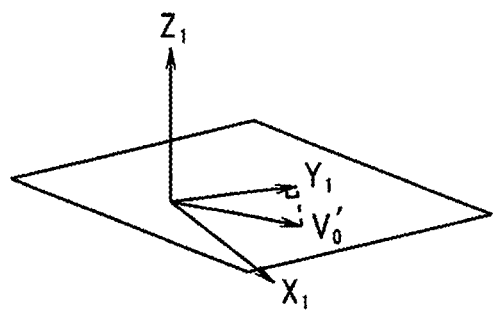
FIG. 33 is an explanatory diagram illustrating a direction vector projected on an intermediate coordinate system $(X_1Y_1Z_1)$.

Further, the rotation matrix $R_{01}$ is determined so that a following condition is satisfied. FIG. 33 is a diagram for illustrating a direction vector projected on the intermediate coordinate system $(X_1Y_1Z_1)$. A condition to be satisfied by the rotation matrix $R_{01}$ is that $Z_1$ is parallel to a gravity direction, and that $V'_0$ is projected to an $X_1Y_1$ plane vertical to $Z_1$, and the projected vector direction and a vector vertical to a $Y_1Z_1$ plane are indicated by $Y_1$ and $X_1$, respectively.

Figure 34:
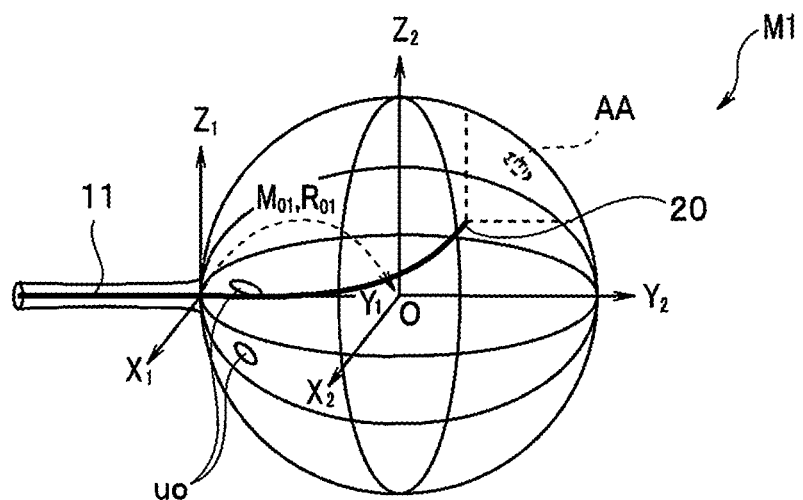
FIG. 34 is an explanatory diagram of a relationship between the intermediate coordinate system $(X_1Y_1Z_1)$ and a second coordinate system $(X_2Y_2Z_2)$.

If position/direction information about the distal end portion 20 is recorded at step S7, the position and direction vectors in the intermediate coordinate system $(X_1Y_1Z_1)$ are further converted to position and direction vectors in the second coordinate system $(X_2Y_2Z_2)$ with a center of the 3D model image M1 as a reference according to next equations (10) and (11), and recorded. FIG. 34 is a diagram for illustrating a relationship between the intermediate coordinate system $(X_1Y_1Z_1)$ and the second coordinate system $(X_2Y_2Z_2)$.

$$P_2 = R_{12}P_1 + M_{02} \quad (10)$$

$$V_2 = R_{12}V_1 \quad (11)$$

Here, $P_1$ and $V_1$ indicate position and direction vectors in the intermediate coordinate system $(X_1Y_1Z_1)$, respectively, and $P_2$ and $V_2$ indicate position and direction vectors in the second coordinate system $(X_2Y_2Z_2)$. $V_2$ indicates a direction vector of a pixel at a center of an endoscopic image in the second coordinate system $(X_2Y_2Z_2)$. $R_{12}$ indicates a rotation matrix shown by a next equation (12), and $M_{02}$ indicates a translation matrix shown by a next equation (13).

[Equation 12]

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} \quad (12)$$

[Equation 13]

$$M_{02} = \begin{pmatrix} m_{x12} \\ m_{y12} \\ m_{z12} \end{pmatrix} \quad (13)$$

Therefore, the point $(x_1, y_1, z_1)$ on the intermediate coordinate system $(X_1Y_1Z_1)$ is converted to a point $(x_2, y_2, z_2)$ on the second coordinate system $(X_2Y_2Z_2)$ as shown by a next equation (14).

[Equation 14]

$$\begin{pmatrix} x_2 \\ y_2 \\ z_2 \end{pmatrix} = \begin{pmatrix} r'_{00} & r'_{01} & r'_{02} \\ r'_{10} & r'_{11} & r'_{12} \\ r'_{20} & r'_{21} & r'_{22} \end{pmatrix} \begin{pmatrix} x_1 \\ y_1 \\ z_1 \end{pmatrix} + \begin{pmatrix} m_{x12} \\ m_{y12} \\ m_{z12} \end{pmatrix} \quad (14)$$

If the $X_1Y_1Z_1$ coordinate system is moved by $R_2$ in a $Y_1$ axis direction, translation $M_{12}$ and rotation $R_{12}$ are as shown by Equations (15) and (16), respectively.

[Equation 15]

$$M_{12} = \begin{pmatrix} m_{x12} \\ m_{y12} \\ m_{z12} \end{pmatrix} = \begin{pmatrix} 0 \\ -R_2 \\ 0 \end{pmatrix} \quad (15)$$

[Equation 16]

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} = \begin{pmatrix} 1 & 0 & 0 \\ 0 & 1 & 0 \\ 0 & 0 & 1 \end{pmatrix} \quad (16)$$

As described above, the position $P_0$ in the first coordinate system $(X_0Y_0Z_0)$ of the magnetic field generating apparatus 9 is converted to the position $P_2$ in the second coordinate system $(X_2Y_2Z_2)$ with the center of the 3D model as a reference by the equations (8) and (14), and the direction $V_0$ in the first coordinate system $(X_0Y_0Z_0)$ is converted to the direction $V_2$ in the second coordinate system $(X_2Y_2Z_2)$ according to next Equation (17).

$$V_2 = R_{12}R_{01}V_0 \quad (17)$$

Further, description will be made on calculation of coordinates in a case of pasting an endoscopic image on the inner surface of the 3D model image M1 in the second coordinate system $(X_2Y_2Z_2)$, in the endoscopic image pasting process at step S14.

Figure 35:
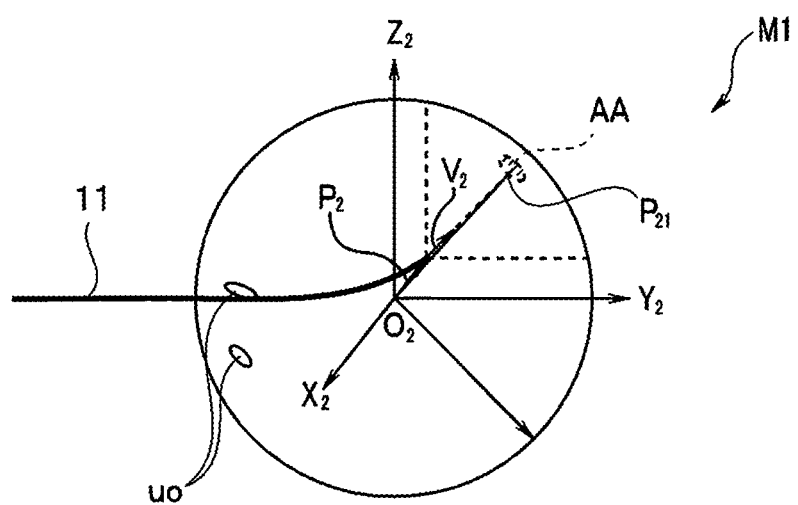
FIG. 35 is an explanatory diagram of coordinates on an inner surface of a sphere of the second coordinate system $(X_2Y_2Z_2)$.
Figure 36:
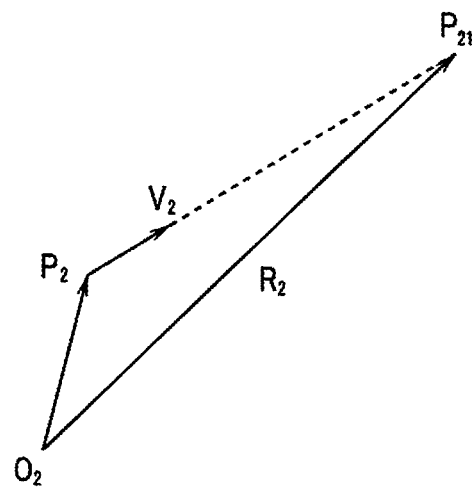
FIG. 36 is an explanatory diagram illustrating a position $P_2$ and a direction vector $V_2$ in the second coordinate system $(X_2Y_2Z_2)$ from a position and direction vector of a distal end portion.

The 3D model M1 assumes that a shape of the urinary bladder B is a sphere with a radius of R2. An endoscopic image is pasted on an inner surface of the sphere. FIG. 35 is a diagram for illustrating coordinates on the inner surface of the sphere of the second coordinate system $(X_2Y_2Z_2)$. FIG. 36 is a diagram for illustrating the position $P_2$ and the direction $V_2$ in the second coordinate system $(X_2Y_2Z_2)$ from the position and direction vectors of the distal end portion 20.

When the position $P_2$ and the direction $V_2$ of the distal end portion 20 in the second coordinate system $(X_2Y_2Z_2)$ are decided, coordinates of the acquired endoscopic image on the inner surface of the sphere are determined. Therefore, a coefficient k satisfying next equations (18) and (19) is calculated, and coordinates $P_{21}$ in the second coordinate system $(X_2Y_2Z_2)$ are determined.

$$P_{21} = P_2 \pm kV_2 \quad (18)$$

$$|P_{21}| = R_2 \quad (19)$$

The endoscopic image is projected and pasted at a position of the determined coordinates $P_{21}$.

Next, the position in the second coordinate system $(X_2Y_2Z_2)$ is projected to a coordinate system of a 2D model.

First, in a case of a hemisphere on the abdomen side of the urinary bladder B $(0 \leq Z_2)$, right and left of the two-dimensional urinary bladder model are reversed. Therefore, a value in a u direction is shown by a next equation (20), and a value in a v direction is shown by a next equation (21).

$$u = -x_{21} \quad (20)$$

$$v = y_{21} + R_2 \quad (21)$$

Further, in a case of a hemisphere on the back side of the urinary bladder B $(Z_2 < 0)$, right and left of the two-dimensional urinary bladder model are reversed. Therefore, a value in the u direction is shown by a next equation (22), and a value in the v direction is shown by a next equation (23).

$$u = -x_{21} \quad (22)$$

$$v = y_{21} - 2R_2 \quad (23)$$

Figure 37:
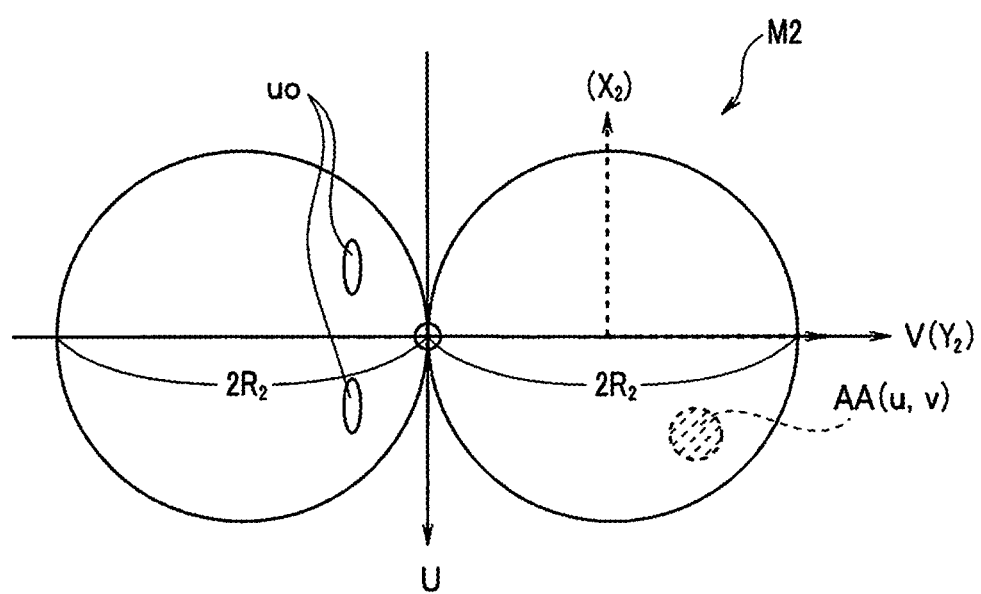
FIG. 37 is an explanatory diagram of a coordinate relationship in a two-dimensional coordinate system (U, V)

FIG. 37 is a diagram for illustrating a coordinate relationship in a two-dimensional coordinate system (U, V).

The direction vector $V_2$ is a direction vector of a pixel at a center of an endoscopic image in the second coordinate system $(X_2Y_2Z_2)$ as described above. Therefore, as for pixels other than the pixel at the center of the endoscopic image, a direction vector of each pixel is determined, and the conversion operations from the equations (18) to (23) described above are repeated. Thereby, it is possible to paste the whole endoscopic image to the inner surface of the sphere of the second coordinate system $(X_2Y_2Z_2)$.

Figure 38:
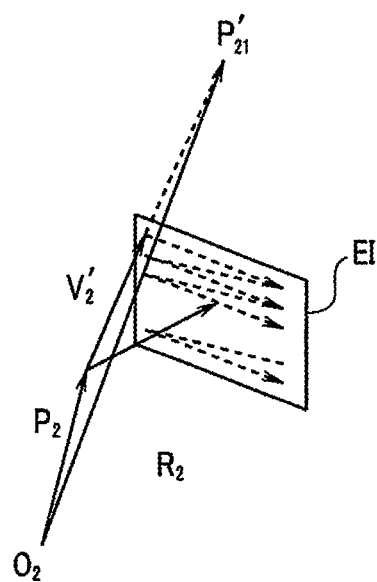
FIG. 38 is an explanatory diagram illustrating scanning of the whole endoscopic image to paste each pixel to the inner surface of the sphere of the second coordinate system $(X_2Y_2Z_2)$.

FIG. 38 is a diagram for illustrating scanning of the whole endoscopic image to paste each pixel to the inner surface of the sphere of the second coordinate system $(X_2Y_2Z_2)$.

Pasting of each pixel of an endoscopic image EI onto the inner surface of the sphere of the second coordinate system $(X_2Y_2Z_2)$ is performed while scanning is performed in a predetermined direction as shown by a dotted line. In FIG. 38, $V_2'$ indicates a pasting vector of each pixel of the endoscopic image EI, and $P_{21}'$ indicates a pasting vector of the inner surface of the sphere of the second coordinate system $(X_2Y_2Z_2)$.

As described above, according to the present embodiment, when an endoscopic image (or picked-up image) obtained by picking up the inside of the urinary bladder B by the image pickup means is pasted (overlapped) and presented (displayed) at a corresponding position on a developed image BE as a planar model image, the presentation is performed in a manner that a correspondence relationship between both images are easily grasped, and, therefore, the surgeon can smoothly perform examination and diagnosis of a site of interest such as a diseased part in the predetermined organ.

Further, since the pasted image judging section 31f as the image pasting judging means for judging whether or not an endoscopic image (or picked-up image) picked up by the image pickup means is an image appropriate for pasting as an image to be pasted on a developed image BE as a planar model image is provided, it is possible to paste an image appropriate for pasting, and the surgeon can smoothly perform examination and diagnosis of a site of interest such as a diseased part in a predetermined organ such as the urinary bladder B.

Further, in the present embodiment, it is possible for a user such as a surgeon to, when presenting an endoscopic image (or picked-up image) picked up by the image pickup means as a pasted image pasted on a developed image BE as a planar model image, to select a method for presenting correspondence between both images in a manner that the correspondence can be easily recognized, and the like from among a plurality of items by the presentation selecting section 38a as presentation selecting means.

Furthermore, according to the endoscope system of the present embodiment described above, since it is possible to easily confirm a position of a lesioned part in the urinary bladder B and an area which is being observed, it is possible to avoid missing of a lesioned part, and it is also possible to lower a reexamination rate and reduce write-down mistakes in a medical record.

Furthermore, though an endoscopic image is pasted on a two-dimensional organ model image in the embodiment described above, the endoscopic image may be pasted on a three-dimensional organ model image, which is a 3D image. That is, the model image may be a 3D image instead of a 2D image.

Furthermore, though an endoscopic image of the inside of the urinary bladder B is pasted onto a 2D model image of the urinary bladder in the embodiment described above, the endoscope system of the embodiment described above is applicable to organs other than the urinary bladder, for example, a stomach and a womb.

Reference information can be decided from change made in an image to perform pasting onto an organ model image when an endoscope enters the stomach from an esophagus in a case of a stomach, when the endoscope comes to a position where a trachea branches to right and left bronchial tubes first at a lower part of the trachea in a case of a lung, or when the endoscope enters the womb from a uterine cervix in a case of a womb and the like.

What is claimed is:

1. An endoscope system comprising:
   an insertion portion configured to be inserted into a predetermined luminal organ in a subject;
   an image sensor provided in a vicinity of a distal end of the insertion portion, wherein the image sensor is configured to pick up an image of an inside of the predetermined luminal organ; and
   a processor comprising hardware, wherein the processor is configured to:
   acquire position information and gaze information about the image sensor;
   generate a planar model image by planarly developing an inner surface of a three-dimensional model image corresponding to the predetermined luminal organ;
   judge whether or not an endoscopic image obtained by picking up the image of the inside of the predetermined luminal organ by the image sensor conforms to a pasting condition;
   paste, as a pasted image, the endoscopic image judged to conform to the pasting condition, on the planar model image, based on the position information and gaze information about the image sensor; and
   present an image pickup range of the image sensor on the planar model image on which the pasted image is pasted based on the position information about the image sensor.

2. The endoscope system according to claim 1, wherein the processor is configured to change an angle for presenting the endoscopic image pasted, as the pasted image, on the planar model image based on the position information and the gaze information about the image sensor.

3. The endoscope system according to claim 1, wherein the processor is configured to change a method for presentation of the pasted image on the planar model image according to a kind of the image sensor.

4. The endoscope system according to claim 1, wherein the processor is configured to perform presentation of the pasted image so that a position of the pasted image in the planar model image is located at a center of the planar model image, based on the position information about the image sensor.

5. The endoscope system according to claim 1, wherein the insertion portion comprises a bendable bending portion provided at the distal end of the insertion portion,
   wherein the image sensor is provided in a vicinity of a distal end of the bendable bending portion, and
   wherein the processor is configured to:
   cause the endoscopic image to be displayed on a display; and
   perform adjustment so that orientations of the endoscopic image displayed on the display and of the pasted image pasted on the planar model image are caused to correspond to each other, according to a bending state of the image sensor accompanying bending of the bendable bending portion.

6. The endoscope system according to claim 1, wherein the processor is configured to:
   generate the three-dimensional model image corresponding to the predetermined luminal organ in addition to the planar model image;

detect information about an insertion shape of the insertion portion being inserted into the predetermined luminal organ; and present the information about the insertion shape in association with the three-dimensional model image corresponding to the predetermined luminal organ.

7. The endoscope system according to claim 1, wherein, when pasting a next picked-up image after pasting the image picked up by the image pickup section at a corresponding position on the planar model image as a picked-up image and as a first pasted image so that the picked-up image substantially corresponds to an area corresponding to the picked-up image, the image pasting/presentation processing section changes the first pasted image to a reduced pasted image.

8. The endoscope system according to claim 1, further comprising: an image display apparatus displaying the picked-up image picked up by the image pickup section and the planar model image in a first display area and a second display area different from each other, respectively, on a same display screen; and a presentation angle adjusting section adjusting an orientation or an angle of the surface model image so that, relative to upward, downward, right and left directions in a case of the picked-up image being displayed in the first display area, upward, downward, right and left directions of the image pasted on the planar model image displayed in the second display area by the image pasting/presentation processing section correspond, respectively, on the display screen.

9. The endoscope system according to claim 1,
wherein the processor is configured to:
    judge whether or not a next endoscopic image, obtained by picking up a next image of the inside of the predetermined luminal organ by the image sensor, conforms to the pasting condition;
    paste, as a next pasted image, the next endoscopic image judged to conform to the pasting condition, on the planar model image; and
    at a time of pasting the next pasted image on the planar model image, reduce a side of the pasted image pasted on the planar model image.

10. The endoscope system according to claim 1,
wherein the processor is configured to:
    control a display to display the endoscopic image in a first display area and the planar model image having the pasted image pasted thereon in a second display area; and
    adjust an orientation or an angle of the planar model image so that, relative to upward, downward, right and left directions in a case of the endoscopic image being displayed in the first display area, and upward, downward, right and left directions of the pasted image pasted on the planar model image displayed in the second display area correspond, respectively, on the display.

11. The endoscope system according to claim 1,
wherein the processor is configured to:
    calculate a distance from the image sensor to an inner wall of the predetermined luminal organ based on the position information and the gaze information about the image sensor;
    calculate an angle formed by a direction of a normal line of the inner wall and a gaze direction of the image sensor based on the position information and the gaze information about the image sensor; and
    judge that the endoscopic image conforms to the pasting condition when the distance from the image sensor to the inner wall of the predetermined luminal organ is within a predetermined range, and the angle formed by the direction of the normal line of the inner wall and the gaze direction of the image sensor is small than a predetermined threshold value.

* * * * *

UNITED STATES PATENT AND TRADEMARK OFFICE
CERTIFICATE OF CORRECTION

| | | |
|---|---|---|
| PATENT NO. | : 10,413,157 B2 | Page 1 of 1 |
| APPLICATION NO. | : 15/080768 | |
| DATED | : September 17, 2019 | |
| INVENTOR(S) | : Miho Minamizato et al. | |

It is certified that error appears in the above-identified patent and that said Letters Patent is hereby corrected as shown below:

On the Title Page

Under abstract "11 Claims, 34 Drawing Sheets" should read --12 Claims, 34 Drawing Sheet--.

In the Claims

Column 33, Lines 7 to 29, Claims 7 and 8 should be deleted.

Column 33, Line 30, Claim 9 should be renumbered as Claim 7.

Column 34, Line 4, Claim 10 should be renumbered as Claim 8.

Column 34, Line 18, insert Claims 9 and 10, as follows:
--9. The endoscope system according to claim 1,
    wherein the processor is configured to judge that the endoscopic image conforms to the pasting condition when the endoscopic image is not determined to be any of a blurred image, a reddish image, a camera-shaken image, and an image in which a plurality of wall surfaces are shown.
10. The endoscope system according to claim 1,
    wherein the processor is configured to:
        calculate an amount of movement of the image sensor based on the position information and the gaze information about the image sensor;
        calculate a moving speed of the image sensor based on the position information and the gaze information about the image sensor;
        calculate a rotation speed of the image sensor around a longitudinal axis based on the position information and the gaze information about the image sensor; and
        judge that the endoscopic image conforms to the pasting condition when the amount of movement of the image sensor is smaller than a first threshold value, the moving speed of the image sensor is smaller than a second threshold value, and the rotation speed of the image sensor around the longitudinal axis is small than a third threshold.--.

Signed and Sealed this
Fifteenth Day of September, 2020

Andrei Iancu
*Director of the United States Patent and Trademark Office*